US009540693B2

(12) United States Patent
Brice et al.

(10) Patent No.: US 9,540,693 B2
(45) Date of Patent: *Jan. 10, 2017

(54) MUTATIONS OF THE PARKIN GENE, COMPOSITIONS, METHODS AND USES

(71) Applicants: Aventis Pharma S.A., Antony (FR); Institut National de la Santé et de la Recherche Médicale, Paris (FR)

(72) Inventors: Alexis Brice, Paris (FR); Christophe Lucking, Paris (FR); Patrice Denefle, Saint Maur (FR); Sylvain Ricard, Paris (FR); Nacer Eddine Abbas, Paris (FR); Sandrine Bouley, Bletterans (FR)

(73) Assignees: Aventis Pharma S.A., Antony (FR); Institut National de la Santé et de la Recherche Médicale, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 14/454,026

(22) Filed: Aug. 7, 2014

(65) Prior Publication Data

US 2015/0074836 A1  Mar. 12, 2015

Related U.S. Application Data

(60) Continuation of application No. 13/209,495, filed on Aug. 15, 2011, now Pat. No. 8,835,618, which is a division of application No. 09/856,290, filed as application No. PCT/FR99/02833 on Nov. 18, 1999, now Pat. No. 7,998,667.

(60) Provisional application No. 60/124,239, filed on Mar. 12, 1999.

(30) Foreign Application Priority Data

Nov. 19, 1998 (FR) ...................................... 98/14524
Aug. 4, 1999 (FR) ...................................... 99/10140

(51) Int. Cl.
C12Q 1/68 (2006.01)
C12N 9/00 (2006.01)
C07K 16/40 (2006.01)

(52) U.S. Cl.
CPC ............ C12Q 1/6883 (2013.01); C07K 16/40 (2013.01); C12N 9/93 (2013.01); C12Q 2600/156 (2013.01); C12Q 2600/16 (2013.01); C12Y 603/02019 (2013.01)

(58) Field of Classification Search
CPC ....................... C12Q 1/6883; C12Q 2600/156
See application file for complete search history.

(56) References Cited

U.S. PATENT DOCUMENTS

| 5,814,491 | A | 9/1998 | Vijg et al. |
| 5,817,478 | A | 10/1998 | Tohda et al. |
| 6,716,621 | B1 | 4/2004 | Shimizu |
| 7,998,667 | B1* | 8/2011 | Brice et al. .................. 435/6.12 |
| 2005/0003385 | A1 | 1/2005 | Shimizu |

FOREIGN PATENT DOCUMENTS

| CA | 2320220 | 8/1999 |
| EP | 1063294 | 12/2000 |
| WO | 9940191 | 8/1999 |

OTHER PUBLICATIONS

Database WPI, Section Ch, Week 199941, Derwent Publications Ltd., London, GB; Jun. 9, 1999.
Search Report for WO00/31253.
Hattori, Nobutaka, et al. "Point Mutations (Thr240Arg and Ala311Stop) in the Parkin Gene." *Biochemical and biophysical research communications* 249.3 (1998): 754-758.
Hattori, Nobutaka, et al. "Molecular genetic analysis of a novel Parkin gene in Japanese families with autosomal recessive juvenile parkinsonism: evidence for variable homozygous deletions in the Parkin gene in affected individuals." *Annals of neurology* 44.6 (1998): 935-941.
Matsumine, Hiroto, et al. "A microdeletion of D6S305 in a family of autosomal recessive juvenile parkinsonism (PARK2)." *Genomics* 49.1 (1998): 143-146.
Shimizu, N., et al. "Sequencing analysis of deletion mutations in the giant Parkin gene." American Journal of Human Genetics. vol. 65. No. 4., 1999.
Saito, M. (1999): Mutational analyses and comparison of clinical phenotypes of six families with autosomal recessive juvenile parkinsonism. American Journal of Human Genetics. 65(4): A489.
Leroy, Elisabeth, et al. "Deletions in the Parkin gene and genetic heterogeneity in a Greek family with early onset Parkinson's disease." *Human genetics* 103.4 (1998): 424-427.
Poropat, Renee A., and Garth A. Nicholson. "Determination of gene dosage at the PMP22 and androgen receptor loci by quantitative PCR." *Clinical chemistry* 44.4 (1998): 724-730.
Abbas, Nacer, et al. "A wide variety of mutations in the parkin gene are responsible for autosomal recessive parkinsonism in Europe." *Human molecular genetics* 8.4 (1999): 567-574.
Translation of Final Office Action of JP No. 2000-584062.
Tassin, Johann, et al. "Chromosome 6—linked autosomal recessive early-onset Parkinsonism: linkage in European and Algerian families, extension of the clinical spectrum, and evidence of a small homozygous deletion in one family." *The American Journal of Human Genetics* 63.1 (1998): 88-94.
EMBL Acc. No. AB009973, Shimizu et al., 1998.
Kitada, Tohru, et al. "Mutations in the parkin gene cause autosomal recessive juvenile parkinsonism." *Nature* 392.6676 (1998): 605-608.
Translation of Non-Final Office Action of JP No. 2000-584062.
Translation of Office Action of CA No. 2351567.
Lucking, C. B., et al. "Homozygous deletions in parkin gene in European and North African families with autosomal recessive juvenile parkinsonism." *Lancet* 352.9137 (1998): 1355-1356.

* cited by examiner

*Primary Examiner* — Jon E Angell
(74) *Attorney, Agent, or Firm* — Lathrop & Gage LLP; James H. Velema, Esq.; Sean M. Coughlin, Esq.

(57) ABSTRACT

The invention concerns nucleic acids coding for mutated or truncated forms of the human parkin gene, or forms comprising multiplication of exons, and the corresponding proteins and antibodies. The invention also concerns methods and kits for identifying mutations of the parkin gene, and for studying compounds for therapeutic purposes.

18 Claims, 5 Drawing Sheets

Figure 2:
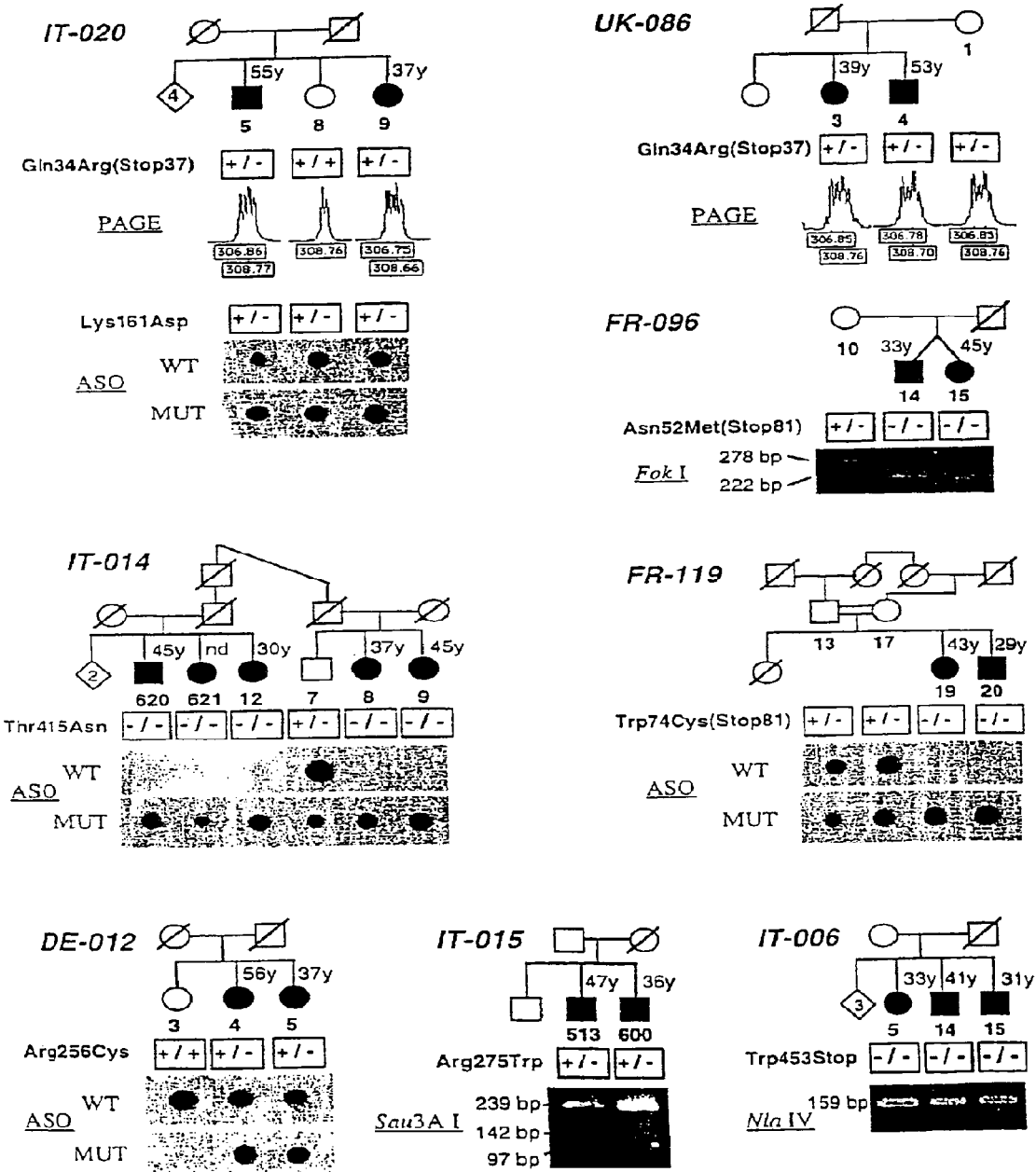

```
  1 tccgggagga ttacccagga gaccgctggt gggaggcgcg gctggcgccg ctgcgcgcat
                                                         Ex1/Ex2
 61 gggcctgttc ctggcccgca gccgccacct acccagtgac catgatag/tg tttgtcaggt 121 tcaactccag ccatggtttc ccagtggagg tcgattctga caccagcatc ttccagctca 181 aggaggtggt tgctaagcga caggggttc cggctgacca gttgcgtgtg attttcgcag
                                                         Ex2/Ex3
241 ggaaggagct gaggaatgac tggactgtgc ag/aattgtga cctggatcag cagagcattg 301 ttcacattgt gcagagaccg tggagaaaag gtcaagaaat gaatgcaact ggaggcgacg 361 accccagaaa cgcggcggga ggctgtgagc gggagcccca gagcttgact cgggtggacc 421 tcagcagctc agtcctccca ggagactctg tggggctggc tgtcattctg cacactgaca
                                                         Ex3/Ex4
481 gcaggaagga ctcaccacca gctggaagtc cag/caggtag atcaatctac aacagctttt 541 atgtgtattg caaaggcccc tgtcaaagag tgcagccggg aaaactcagg gtacagtgca
                                                         Ex4/Ex5
601 gcacctgcag gcaggcaacg ctcaccttga cccag/ggtcc atcttgctgg gatgatgttt
                                                         Ex5/Ex6
661 taattccaaa ccggatgagt ggtgaatgcc aatccccaca ctgccctggg actagtgca/g 721 aatttttctt taatgtgga gcacaccca cctctgacaa ggaaacatca gtagctttgc
                                                         Ex6/Ex7
781 acctgatcgc aacaaatagt cggaacatca cttgcattac gtgcacagac gtcag/gagcc 841 ccgtcctggt tttccagtgc aactcccgcc acgtgatttg cttagactgt ttccacttat 901 actgtgtgac aagactcaat gatcggcagt ttgttcacga ccctcaactt ggctactccc
               Ex7/Ex8
961 tgccttgtgt gg/ctggctgt cccaactcct tgattaaaga gctccatcac ttcaggattc
               Ex8/Ex9
1021 tgggagaaga gcag/tacaac cggtaccagc agtatggtgc agaggagtgt gtcctgcaga 1081 tgggggggcgt gttatgcccc cgccctggct gtggagcggg gctgctgccg gagcctgacc
                                                         Ex9/Ex10
1141 agaggaaagt cacctgcgaa ggggcaatg gcctggctg tggg/tttgcc ttctgccggg 1201 aatgtaaaga agcgtaccat gaaggggagt gcagtgccgt atttgaagcc tcaggaacaa
                Ex10/Ex11
1261 ctactcag/gc ctacagagtc gatgaaagag ccgccgagca ggctcgttgg gaagcagcct 1321 ccaaagaaac catcaagaaa accaccaagc cctgtccccg ctgccatgta ccagtggaaa
                Ex11/Ex12
1381 aaaatg/gagg ctgcatgcac atgaagtgtc cgcagcccca gtgcaggctc gagtggtgct
                                                                stop
1441 ggaactgtgg ctgcgagtgg aaccgcgtct gcatggggga ccactggttc gacgtgtagc
```

Figure 1

```
1501 cagggcggcc gggcgcccca tcgccacatc ctgggggagc atacccagtg tctaccttca
1561 ttttctaatt ctcttttcaa acacacacac acacgcgcgc gcgcgcacac acactcttca
1621 agtttttttc aaagtccaac tacagccaaa ttgcagaaga aactcctgga tccctttcac
1681 tatgtccatg aaaaacagca gagtaaaatt acagaagaag ctcctgaatc cctttcagtt
1741 tgtccacaca agacagcaga gccatctgcg acaccaccaa caggcgttct cagcctccgg
1801 atgacacaaa taccagagca cagattcaag tgcaatccat gtatctgtat gggtcattct
1861 cacctgaatt cgagacaggc agaatcagta gctggagaga gagttctcac atttaatatc
1921 ctgccttta ccttcagtaa acaccatgaa gatgccattg acaaggtgtt tctctgtaaa
1981 atgaactgca gtgggttctc caaactagat tcatggcttt aacagtaatg ttcttattta
2041 aattttcaga aagcatctat tcccaaagaa ccccaggcaa tagtcaaaaa catttgttta
2101 tccttaagaa ttccatctat ataaatcgca ttaatcgaaa taccaactat gtgtaaatca
2161 acttgtcaca aagtgagaaa ttatgaaagt taatttgaat gttgaatgtt tgaattacag
2221 ggaagaaatc aagttaatgt actttcattc cctttcatga tttgcaactt tagaaagaaa
2281 ttgtttttct gaaagtatca ccaaaaaatc tatagtttga ttctgagtat tcattttgca
2341 acttggagat tttgctaata catttggctc cactgtaaat ttaatagata aagtgcctat
2401 aaaggaaaca cgtttagaaa tgatttcaaa atgatattca atcttaacaa aagtgaacat
2461 tattaaatca gaatctttaa agaggagcct ttccagaact accaaaatga agacacgccc
2521 gactctctcc atcagaaggg tttatacccc tttggcacac cctctctgtc caatctgcaa
2581 gtcccaggga gctctgcata ccaggggttc cccaggagag accttctctt aggacagtaa
2641 actcactaga atattcctta tgttgacatg gattggattt cagttcaatc aaactttcag
2701 cttttttttc agccattcac aacacaatca aaagattaac aacactgcat gcggcaaacc
2761 gcatgctctt acccacacta cgcagaagag aaagtacaac cactatcttt tgttctacct
2821 gtattgtctg acttctcagg aagatcgtga acataactga gggcatgagt ctcactagca
2881 catggaggcc cttttggatt tagagactgt aaattattaa atcggcaaca gggcttctct
2941 ttttagatgt agcactgaaa
```

Figure 1 (continued)

MUTATIONS OF THE PARKIN GENE, COMPOSITIONS, METHODS AND USES

RELATED APPLICATIONS

This application is a continuation of U.S. patent application Ser. No. 13/209,495, filed Aug. 15, 2011, now U.S. Pat. No. 8,835,618 issued Sep. 16, 2014, which is a divisional of U.S. patent application Ser. No. 09/856,290 filed Aug. 13, 2001, now U.S. Pat. No. 7,998,667, issued Aug. 16, 2011, which is a National Stage Entry under 37 U.S.C. 371 of PCT/FR99/02833 filed Nov. 18, 1999, which claims the benefit of priority to U.S. Provisional Patent Application No. 60/124,239, filed Mar. 12, 1999, and also claims priority to FR99/10140 filed Aug. 4, 1999 and FR98/14524 filed Nov. 19, 1998, the contents of each of which are hereby incorporated by reference in their entirety.

The present invention relates to the field of genetics and, more particularly, to the identification of mutations in the parkin gene. It also relates to compositions and methods for the identification of these mutations in samples, mutated or truncated forms of parkin or forms comprising exon multiplications, and their uses for diagnostic, screening or therapeutic purposes, for example.

Parkinson's disease is a frequent neurodegenerative condition whose prevalence is close to 2% after the age of 65 [de Rijk et al., 1997]. The cardinal signs of the disease are rigidity, bradykinesia, rest tremor and good reactivity, at least initially, to levodopa. The disorders are due to a massive loss of dopaminergic neurons from the substantia nigra. The causes of the disease remain unknown, but the involvement of factors for genetic susceptibility is strongly suspected [Wood, 1997]. Many familial forms with dominant transmission have been reported. Mutations in the gene encoding alpha-synuclein, located at 4q21-q23, have been described in a small number of families with an early onset and a rapid deterioration [Polymeropoulos et al., 1997; Krüger et al., 1998]. A second locus is situated at 2p13 [Gasser et al., 1998]. A parkinsonian syndrome with autosomal-recessive transmission (AR-JP) has been described in Japan [Yamamura et al., 1973; Ishikawa and Tsuji, 1996]. It manifests itself with the cardinal signs of Parkinson's disease with certain specific features: i) early onset, as a rule before the age of 40; ii) presence of a dystonia, often at the lower limbs; iii) fluctuations during the day; and iv) slow progressive evolution but always associated with dyskinesias under levodopa. Neuropathological examination reveals a massive loss of neurons from the substantia nigra pars compacta but without Lewy bodies, a histopathological stigma of idiopathic Parkinson's disease [Yamamura et al., 1973; Takahashi et al., 1994]. A genetic linkage between the disease in Japanese families and 6q25.2-27 markers has been demonstrated which defines the PARK2 locus [Matsumine et al., 1997]. Two teams then described PARK2 families outside Japan, in particular in the United States, in Europe and in the Middle East [Jones et al., 1998; Tassin et al., 1998]. Very recently, Kitada et al. [Kitada et al., 1998] have identified deletions of exons (3-7) or of exon 4 in a new gene, called parkin, in 4 Japanese families.

The present application now describes the demonstration and characterization, in 77 families and 102 isolated cases, mainly European, having an early-onset parkinsonian syndrome, of the presence of new genetic alterations affecting the parkin gene. In addition, the present application shows that these genetic alterations are present not only in early-onset parkinsonian syndromes, but also in more tardive or atypical parkinsonian syndromes. These new alterations therefore offer new tools both for the diagnosis and the treatment of Parkinson's disease.

A more particular subject of the invention relates to a nucleic acid encoding human parkin, characterized in that it contains one or more genetic alterations chosen from:
a) a deletion of one or more exons, in combination or otherwise,
b) a multiplication (e.g. duplication, triplication) of exons,
c) a point mutation,
d) a deletion of 1 or more contiguous base pairs causing a reading frame shift, and
e) an insertion of 1 or more contiguous base pairs.

The term nucleic acid as defined in the present application designates deoxyribonucleic (DNA) and ribonucleic (RNA) acids. In addition, among the DNAs, they may correspond to genomic DNA (gDNA) or complementary DNA (cDNA). The nucleic acids of the invention may be of a natural or synthetic origin. They are generally prepared by conventional molecular biology techniques, including the screening of libraries, artificial synthesis, ligation, restriction, and the like. The positions given in the present application are calculated relative to the sequence of human parkin represented in FIG. 1 (SEQ ID No: 1). This sequence represents the sequence of the cDNA encoding human parkin. Compared with the sequence described by Kitada et al., it contains a modification at the level of nucleotide 768 (C->T).

The genetic alterations a) to e) defined above are mainly exon alterations, that is to say which affect the coding region of the human parkin gene. However, intron alterations, that is to say alterations which affect the non-coding part of the gene, have also been demonstrated.

The human parkin gene comprises 12 exons, the nucleotide positions of which are given below:

| | |
|---|---|
| Exon 1: nucleotides 1 to 108 | Exon 2: nucleotides 109 to 272 |
| Exon 3: nucleotides 273 to 513 | Exon 4: nucleotides 514 to 635 |
| Exon 5: nucleotides 636 to 719 | Exon 6: nucleotides 720 to 835 |
| Exon 7: nucleotides 836 to 972 | Exon 8: nucleotides 973 to 1034 |
| Exon 9: nucleotides 1035 to 1184 | Exon 10: nucleotides 1185 to 1268 |
| Exon 11: nucleotides 1269 to 1386 | Exon 12: nucleotides 1387 to 2960 |

In a first embodiment, the invention relates to a nucleic acid encoding parkin, comprising deletions of one or more exons, in particular combinations of deletions of exons. More particularly, these deletions affect exons 2 to 9 separately or in combination. Particular examples of these deletions and combinations of deletions of exons of the parkin gene are illustrated in Tables 2 and 4. In addition, these deletions may be homozygous, that is to say may affect both chromosomes simultaneously, or heterozygous (incidence on only one chromosome).

The applicant has in particular demonstrated the heterozygous deletion of exon 2 as well as combinations of deletions of this exon with other exons including in particular exon 3 and exon 4. Thus, nine deletions or combinations of deletions have for the first time been demonstrated and in particular the following deletions: exons 2,2+3,2+3+4,3-6, 3-9,6,6+7,7+8+9 and 8. Moreover, these deletions or combinations of deletions may be combined with each other in the case of composite heterozygotes.

The applicant has also identified a number of homozygous deletions, alone or in combinations, such as the deletions of exons 5 and 6.

The particular positions of the deletions described above may be defined with reference to the numbering of the nucleotides in FIG. 1.

In another specific embodiment, the invention relates to a nucleic acid encoding parkin, containing a deletion of exon 3. More particularly, this deletion affects nucleotides 273 to 513 in FIG. 1.

In another specific embodiment, the invention relates to a nucleic acid encoding parkin, comprising a deletion of exons 8 and 9. More particularly, this deletion affects nucleotides 973 to 1184 in FIG. 1.

The consequences of these deletions or combinations of deletions often remain a shift in the reading frame. Table 4 summarizes the consequences which appeared opposite the deletions or combinations of deletions recorded.

In another particular embodiment, the invention relates to a nucleic acid encoding parkin, comprising a multiplication of exons, that is to say the repetition of one or more exons in the gene. The present application shows for the first time, either a homozygous and heterozygous duplication as is illustrated in the examples by the duplication of exon 3, or a duplication of the heterozygous type as illustrated in the duplication of exon 6, 7 or 11. The present application also shows for the first time a triplication of exons: either a homozygous triplication, or a heterozygous triplication as is illustrated in the examples by the triplication of exon 2.

Preferably, the term multiplication of exons indicates the presence of 2 to 5 copies of the exon(s) considered, preferably 2 to 3 copies. Generally each copy of an exon is positioned in the sequence beside the original exon.

In another specific embodiment, the invention relates to a nucleic acid encoding parkin, comprising a point mutation, that is to say the replacement of one base pair with another. The present application indeed shows the existence of point mutants of parkin and the causal character of some of them in the appearance and the development of a parkinsonian syndrome. More particularly, the point mutation(s) according to the invention are nonsense or missense point mutations or mutations causing a reading frame shift.

A nonsense mutation is a mutation which introduces a stop codon into the sequence. Such a mutation leads to the premature termination of translation, and therefore to the synthesis of a truncated protein. Such a mutation is therefore also designated in the text which follows by the term "truncating". More preferably, according to the present invention, the nucleic acid comprises a nonsense mutation located in a region corresponding to the N- or C-terminal domain of human parkin. The present invention indeed shows that this type of mutation occurs in patients more frequently in the terminal regions of the gene (and therefore of the protein). Still more preferably, the present invention relates to a nucleic acid encoding human parkin, comprising a truncating point mutation in a region corresponding to exons 2, 3, 11 or 12. It is more preferably a mutation in exon 12 of the parkin gene, preferably leading to the inactivation of the myristoylation site (residues 450-455 of the protein). By way of illustration, there may be mentioned the point mutation G->A on nucleotide 1459, introducing a stop codon in place of the residue Trp453. This mutant therefore encodes a truncated protein comprising the first 452 amino acids of the wild-type protein. Surprisingly, the applicant has shown that this parkin 1-452 mutant, which lacks only the last 12 residues of the wild-type protein, causes Parkinson's disease.

According to another embodiment, the present invention relates to a nucleic acid encoding human parkin, comprising a truncating point mutation in exon 7. By way of illustration, there may be mentioned the T->A point mutation on nucleotide 905, introducing a stop codon in place of the Cysteine 268 residue.

Another type of point mutation according to the invention is a missense mutation. A missense mutation comprises the replacement of a base pair in a codon, leading to a codon encoding an amino acid different from the natural amino acid, without interruption of the sequence. Such an isolated mutation therefore leads to a protein having an unchanged number of residues, but in which one of the residues differs from the wild-type protein. The present application has now shown that missense point mutants of parkin exist in subjects suffering from parkinsonian syndromes, and that these mutants may have a causal character. More preferably, the invention relates to a nucleic acid encoding human parkin, comprising at least one missense point mutation located especially in a region corresponding to exons 4 to 12 and preferably to exons 4, 6, 7, 9, 11 and 12.

A first type of more specific missense point mutations for the purposes of the invention comprises the mutations which cause a nonconservative change of amino acid in the encoded protein. Such mutations are indeed more specifically associated with the Parkinson's disease phenotype. Nonconservative change is understood to mean the replacement of an amino acid with another amino acid having structural, physicochemical and/or biological properties which are different from the first. Thus, the change of one basic amino acid with a nonbasic amino acid is said to be nonconservative. This type of change comprises, more particularly, the change of the amino acids of one or other of the following categories: acidic, basic, polar neutral, nonpolar neutral. Specific examples of mutants of this type according to the invention are in particular the nucleic acids comprising the following genetic alteration, alone or in combination:

an A->T mutation on nucleotide 584 (Lys161Asp) in exon 4,
an A->T mutation on nucleotide 734 (Lys211Asn) in exon 6,
a C->T mutation on nucleotide 867 (Arg256Cys) in exon 7,
a C->T mutation on nucleotide 924 (Arg275Trp) in exon 7,
a G->A mutation on nucleotide 939 (Asp280Asn) in exon 7,
a G->A mutation on nucleotide 1084 (Gly328Glu) in exon 9,
a C->T mutation on nucleotide 1101 (Arg334Cys) in exon 9, and/or
a G->A mutation on nucleotide 1390 (Gly430Asp) in exon 12.

A second type of more specific missense point mutations for the purposes of the invention comprises conservative mutations. Such mutations cover any replacement of a codon encoding an amino acid with a codon encoding an amino acid of the same group. Amino acid group is understood to mean the amino acids whose structural, physicochemical and/or biological properties are very similar and are defined according to the following categories: acidic, basic, polar neutral, nonpolar neutral. As an example of a conservative mutation, there may be mentioned in general the replacement of the AAA codon (Lys) with the AGA codon (Arg), Lys and Arg forming part of the same group of basic amino acids. A specific example of this type of mutation according to the invention is in particular the nucleic acid comprising the following genetic alteration, alone or in combination:

a T->G mutation on nucleotide 966 (Cys289Gly) in exon 7.

A third type of more specific missense point mutations for the purposes of the invention comprises the mutations which affect a potential phosphorylation site in the encoded protein. The present application indeed shows that mutants of this type appear in some subjects suffering from Parkinson's disease, and therefore constitute events which participate in the development of the pathology, because of the known biological functions of phosphorylation events.

Specific mutations are therefore those which modify a phosphorylatable amino acid to a nonphosphorylatable residue. In this regard, the residues capable of being phosphorylated are, for example, the serine, threonine and tyrosine residues.

Specific examples of mutants of this type according to the invention are in particular the nucleic acids comprising the following genetic alteration, alone or in combination:

C->A mutation on nucleotide 1345 (Thr415Asn), exon 11.

Moreover, as indicated above, the present invention also relates to any nucleic acid comprising a deletion of one or more contiguous base pairs and causing a reading frame shift (see d). The present application demonstrates for the first time the existence of restricted deletion mutants of parkin, and their involvement in the appearance and the development of a parkinsonian syndrome. More preferably, the restricted deletions according to the invention lead, because of the reading frame shift, to the synthesis of proteins (i) which are truncated and (ii) whose C-terminal sequence is different from the wild-type protein. In the case of intron deletions, the reading frame shift may lead either to the nonrecognition of the intron if the mutation takes place at the exon-intron junction and the production of an aberrant protein, or to incorrect folding of the intron, thus preventing its excision-splicing, when the mutation takes place inside the intron. As indicated above, this protein (or the novel domain) constitutes another subject of the present application.

More preferably, the invention relates to the nucleic acids comprising a deletion of 1 to 10 and preferably 1 to 5 contiguous base pairs. Still more particularly, the deletions according to the invention are located in a region of the nucleic acid corresponding to intron 8 or to exon 9 or to a terminal region of the protein, especially in exons 2 or 3, for example to exon 2. By way of a specific example, there may be mentioned a nucleic acid containing the following alterations, alone or in combination:

a deletion of the AG nucleotides at positions 202 and 203. This deletion introduces a change in the reading frame starting at the level of amino acid residue 34 (Gln->Arg), and ending with a stop codon (37). This protein is therefore truncated and comprises a novel C-terminal region of 4 amino acids.

a deletion of the A nucleotide at position 255. This deletion introduces a change in the reading frame starting at the level of amino acid residue 52 (Asn->Met), and ending with a stop codon (81). This protein is therefore truncated and comprises a novel C-terminal region of 30 amino acids.

a deletion of the five base pairs TCTGC in intron 8, at position −21 −17 relative to exon 9 and capable of causing nonrecognition of the splicing site.

a deletion of two base pairs in exon 9 at position 1142-1143delGA which changes Arg348 to Glu. The consequence of this deletion is the introduction of a change in the reading frame, thus creating a stop codon at position 368 in exon 10.

As indicated above, the present invention also relates to a nucleic acid comprising one or more genetic alterations, such as, in particular, an insertion of one or more contiguous base pairs (see d)). The present application indeed demonstrates for the first time the existence of insertion mutants of parkin, and their involvement in the appearance and the development of Parkinson's disease. More preferably, the insertion according to the invention is such that it causes a reading frame shift. Because of this, the insertion causes a change in the residues situated downstream (C-terminal side) of the mutation. In addition, this insertion leads more generally to the creation of a premature stop codon, and therefore to the synthesis of a protein (i) which is truncated and (ii) whose C-terminal sequence is different from the wild-type protein. As indicated later, this protein (or the original domain) constitutes another subject of the present application, and may be used as a diagnostic or therapeutic tool.

More preferably, the invention relates to the nucleic acids comprising an insertion of 1 to 5 contiguous base pairs, preferably 1 or 2. By way of a specific example, there may be mentioned a nucleic acid comprising a GT insertion between nucleotides 321 and 322. This insertion introduces a change in the reading frame starting at the level of the amino acid residue 74 (Trp->Cys), and ending with a stop codon (81). This protein is therefore truncated and comprises a novel C-terminal region of 8 amino acids.

Of course the genetic alterations a) to e) described above may be isolated or combined with each other, such as, in particular, a missense mutation and a deletion or two cumulative missence mutations. By way of examples illustrating this type of combination, there may be mentioned in particular the combination of the following modifications:

a C->T missense mutation at position 1101 (Arg334Cys) in exon 9 with a deletion of 5 base pairs at position −21 −17 relative to exon 9, in intron 8 a C->T missense mutation at position 924 (Arg275Trp) in exon 7 with a G->A missense mutation at position 1390 (Gly430Asp) in exon 12.

The subject of the invention is also a nucleic acid encoding human parkin, characterized in that it comprises the sequence presented in FIG. 1 (SEQ ID No: 1). This sequence contains, compared with the sequence isolated by Kitada et al., a T at position 768, in place of a C, resulting, in the encoded protein, in an amino acid serine at position 223, in place of a proline. This nucleic acid encodes the wild-type parkin found in European populations.

The subject of the invention is also the polymorphic variants of the nucleic acid presented in FIG. 1. The present application indeed shows that the human parkin gene exhibits some polymorphism, and describes more particularly certain variants having more specifically one of the following sequence modifications:

G->A mutation on nucleotide 601 of exon 4 (Ser167Asn)

G->C mutation on nucleotide 1239 of exon 10 (Val380Leu)

G->A mutation on nucleotide 1281 of exon 11 (Asp394Asn).

The invention also relates to any vector comprising a nucleic acid as defined above. It may be a plasmid vector, a cosmid, viral vector, episome, artificial chromosome, and the like. In a specific embodiment, such a vector also comprises a promoter region allowing the expression of said nucleic acid.

Such vectors may be used to produce in large quantities the nucleic acids of the invention, or to produce the corresponding polypeptides, in an appropriate cellular host (prokaryotic, eukaryotic, animal or plant cell, for example). Preferred cellular hosts are in particular bacterial cells (*E. coli* for example) or yeast cells, or alternatively mammalian, animal or human cells.

In this regard, the invention also relates to any recombinant cell containing a nucleic acid or a vector as defined above.

The invention also relates to any mammalian, in particular human, cell containing a nucleic acid or a vector as defined above, as a replacement for the wild-type gene for parkin.

The cells of the invention may be used in particular for studying the properties of parkin, and also as models for the search for compounds capable of compensating for the genetic alterations of the parkin gene.

The invention relates, in addition, to any nonhuman mammal comprising a nucleic acid as defined above in its cells. Advantageously, these mammals are obtained by "knock-in" of the alterations defined above, by homologous recombination, or also by "knock-out" of the wild-type gene, which is replaced by the altered version of the invention.

Such mammals (rodents, canines, rabbits and the like) can in particular be used for studying the properties of parkin and the identification of compounds for therapeutic purposes, for example.

The invention also relates to any polypeptide encoded by a nucleic acid as defined above. These polypeptides are therefore human parkin, its polymorphic variants, and mutated and/or truncated variants and/or variants comprising a multiplication of exons, involved in the appearance and/or development of a parkinsonian syndrome. The invention relates in particular to the truncated or aberrant variants of parkin as described above, or a portion thereof corresponding to the sequence created by the reading frame shift. Such polypeptides or fragments, or the corresponding nucleic acids, can be used for identifying and/or studying compounds capable of restoring a normal phenotype to cells expressing them. In particular, the nucleic acids described above may be transferred into appropriate host cells, preferably eukaryotic cells (mammal, yeast for example), to be used in a test for screening compounds capable of counteracting their activity, whether they are chemical, biochemical or genetic compounds. Such polypeptides or fragments can also be used as antigens, for the preparation of specific antibodies, which can be used for the detection of the variants. In particular, the specific polypeptide regions of the truncated forms (in particular the ends) may be used for the preparation of antibodies; according to conventional immunological techniques, which antibodies then constitute tools for detecting the presence of these forms in biological samples obtained from subjects. Such antibodies may be polyclonal or monoclonal (prepared for example by fusion of spleen cells of animals immunized with the antigens, with myeloma cells, followed by selection of clones producing monoclonal antibodies).

In this regard, the invention also relates to any antibody specific for a polypeptide as described above, or for a specific region of such a polypeptide. The term "specific antibody" designates an antibody having a particularly high affinity for the given antigen, compared with any other antigen.

The invention relates, in addition, to any composition comprising a polypeptide or an antibody or alternatively a vector or a host cell transformed by the nucleic acid of the invention, as described above. These compositions may be packaged in various types of media (isotonic, saline solutions, and the like) in the presence of stabilizers or preservatives, for example. These compositions may be stored at cold temperature or frozen, in any appropriate device (tube, box, bottle, flask, bag and the like).

Moreover, in addition to the genetic exon alterations described above, the invention also describes genetic intron alterations of the parkin gene. These alterations do not induce any change in the sequence of the encoded protein, and essentially constitute polymorphic variants. These variants are more particularly described in Table 2.

One of the applications of the invention consists in the detection of the presence of mutations in the parkin gene, and their correlation with the susceptibility to Parkinson's disease, for example. In this regard, the invention also relates to various tools (probes, primers, antibodies and the like), which are useful for carrying out such detection methods.

In particular, the invention relates to any probe or oligonucleotide which hybridizes specifically with a nucleic acid as defined above.

The specific probes or oligonucleotides of the invention generally comprise less than 500 bp, more preferably less than 300 bp. Typically, a specific oligonucleotide of the invention comprises from 5 to 100 bp, advantageously from 5 to 50 bp. The length of the oligonucleotide may of course be adjusted by persons skilled in the art. The probes or oligonucleotides of the invention are moreover generally labeled, so as to allow their detection. Various types of labelings known to persons skilled in the art may be used (radioactive, fluorescent, enzymatic, chemical, end or internal labeling, and the like). Finally, the probes or oligonucleotides of the invention have the capacity to specifically hybridize with the nucleic acids as defined above, that is to say with the various altered forms of the parkin gene. The hybridization is said to be specific when the probe or oligonucleotide hybridize, under conditions of high stringency, with the nucleic acid carrying the desired alteration, and not or not to any great extent with the same nucleic acid not carrying said alteration. The hybridization is therefore said to be specific when the specific signal/background noise differential is sufficiently high to be detected.

The probes or oligonucleotides of the invention are therefore generally complementary to at, least one region of the parkin gene carrying the genetic alterations a) to d) described above. The complementarity is generally perfect, so as to ensure a better hybridization selectivity. These probes or oligonucleotides may be synthesized by any technique known to persons skilled in the art, for example by cleavage from the nucleic acids described above, or by artificial synthesis, or by combining these techniques. These probes or oligonucleotides can be used for the identification, on biological samples, of the presence of genetic alterations of the parkin gene.

The invention also relates to a pair of primers for the amplification of all or part of a nucleic acid as described above, characterized in that it comprises:
 a first primer complementary to a region of the parkin gene situated in 5' of a genetic alteration, and
 a second primer complementary to a region of the parkin gene situated in 3' of said genetic alteration.

The primers of the invention are generally complementary to a region of the parkin gene, and advantageously comprise less than 30 bp.

The invention further relates to a method for the identification of a genetic alteration in the parkin gene, and in particular the detection of deletion(s) and/or multiplication (e.g. duplication, triplication) of exons in the homozygous and heterozygous state.

This method according to the invention comprises:
i) the provision of a sample comprising the parkin gene,
ii) the amplification (semi-quantitative) of at least a portion of said gene, said portion comprising a genetic alteration as defined above, and
iii) the detection of the presence of the genetic alteration.

Advantageously, in the method of the invention, the sample is a sample of blood, tissue, plasma or a cell culture, obtained from a subject, in particular from a mammal, in particular from a human. In a preferred embodiment, the sample is pretreated so as to make the parkin gene, or a portion thereof, accessible for the amplification. This pretreatment may comprise the lysis of the cells, an enzymatic treatment, a denaturation, and the like.

Advantageously, the amplification is carried out by means of a pair of primers as described above or those described by Kitada et al. and included by way of reference.

By way of a specific example of a pair of primers according to the invention, there may be mentioned the primers serving for the detection of alterations in exon 3 or of point mutations. Thus, the following pair of primers was used in the context of the invention:

```
For:
                                      (SEQ ID No: 2)
5'-(Hex)AATTGTGACCTGGATCAGC-3'
and Rev:
                                      (SEQ ID No: 3)
5'-CTGGACTTCCAGCTGGTGGTGAG-3'
```

The following primers were also used for the detection of the following point mutations:

```
Asp280Asn:
                                      (SEQ ID No: 4)
5'-GGCAGGGAGTAGCCAAGTTGAGGAT-3'
wild-type sequence G Arg334Cys:
                                      (SEQ ID No: 5)
5'-AGCCCCGCTCCACAGCCAGCGC-3'
wild-type sequence G
```

The detection of a genetic alteration as described above may be carried out by various techniques, and in particular by sequencing, PCR/restriction, ASO, PAGE or by semi-quantitative multiplex PCR, as detailed in the experimental part. Briefly, this method is based on semi-quantitative PCR amplification and in the exponential phase of template DNA. According to this method, comparison of the relative level of template DNA is sufficient to demonstrate a loss of the quantity of DNA (deletion of exon(s)) or on the contrary an increase in the quantity of DNA (multiplication of exon(s)).

The invention relates, in addition, to a kit for carrying out the methods of the invention, comprising a probe or an oligonucleotide or a pair of primers as described above. The kits of the invention advantageously comprise the appropriate reagents for an amplification and/or hybridization reaction, and, optionally, a support for such reactions (filters, membranes, chips and the like).

The present invention is particularly appropriate for the diagnosis of a susceptibility to Parkinson's disease, by the search for a genetic alteration as described above in the parkin gene.

The present invention also relates to the use of the tools described above (nucleic acids, probes, polypeptides, antibodies, cells, animals) for the identification of compounds capable of counteracting, at least in part, the effects of a genetic alteration in the parkin gene, in particular with a therapeutic objective. Thus, such compounds may be detected by bringing into contact with a test composition (or product) in the presence of a cell or an animal as described above, and detecting a phenotypic or genotypic effect.

The method of the invention may in particular allow the identification of compounds which can be used, alone or in combination with other products or treatments, for treating (i.e. reducing) Parkinson's disease. Such compounds constitute another subject of the present invention.

Other advantages and applications of the present invention will emerge on reading the following examples which should be considered as illustrative and nonlimiting.

EXAMPLES

A—Legend to the Figures

FIG. 1: cDNA sequence encoding human parkin. The junctions between the exons are indicated. The initiator codon (atg) and the stop codon (tag) are in bold. The C>T change at position 768 is in bold and underlined.

FIG. 2: Families having point mutations in the parkin gene. The complete cosegregation of the mutation with the disease is represented. The black squares (men) and circles (women) represent the individuals affected with the age of appearance (in years) indicated under the symbol for the patient. The crossed symbols indicate deceased patients. The number of nonaffected and nonanalyzed brothers and sisters is given as a diamond. For each mutation (change in amino acid), the genotype of the family member is indicated (+/+ wild-type homozygote, +/− heterozygous for the mutation; −/− homozygous for the mutation). Under each genotype, the detection results are given. PAGE: electrophoretogram with the size of the allele in bp; ASO: autoradiograms of the mutated and wild-type alleles; PCR/restriction: PCR products after digestion with the appropriate restriction enzymes. The length of the fragments in by is given. Mut: mutated; nd: age of appearance not determined, since the patient is not conscious of the symptoms.

Figure 3:
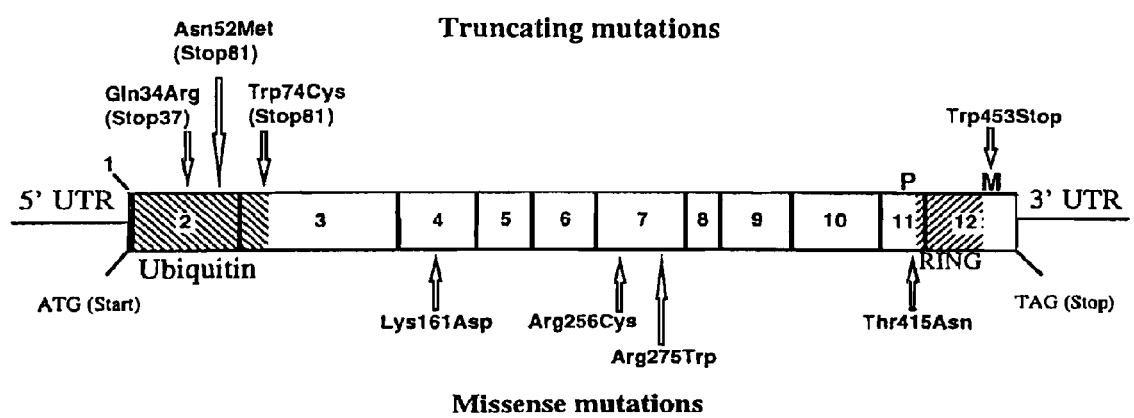

FIG. 3: Representation and location of the point mutations in the parkin gene. The coding sequence of the gene, with its 12 exons, is represented (bar). The exons are numbered 1 to 12. The 8 causal point mutations are positioned according to their effect on the protein (truncation vs missense). The ubiquitin-like domain and the ring motif ("Ring Finger") are hatched. For the Thr415Asn and Trp453Stop mutations, the phosphorylation (P) and myristoylation (M) sites are indicated. UTR; untranslation region.

Figure 4:
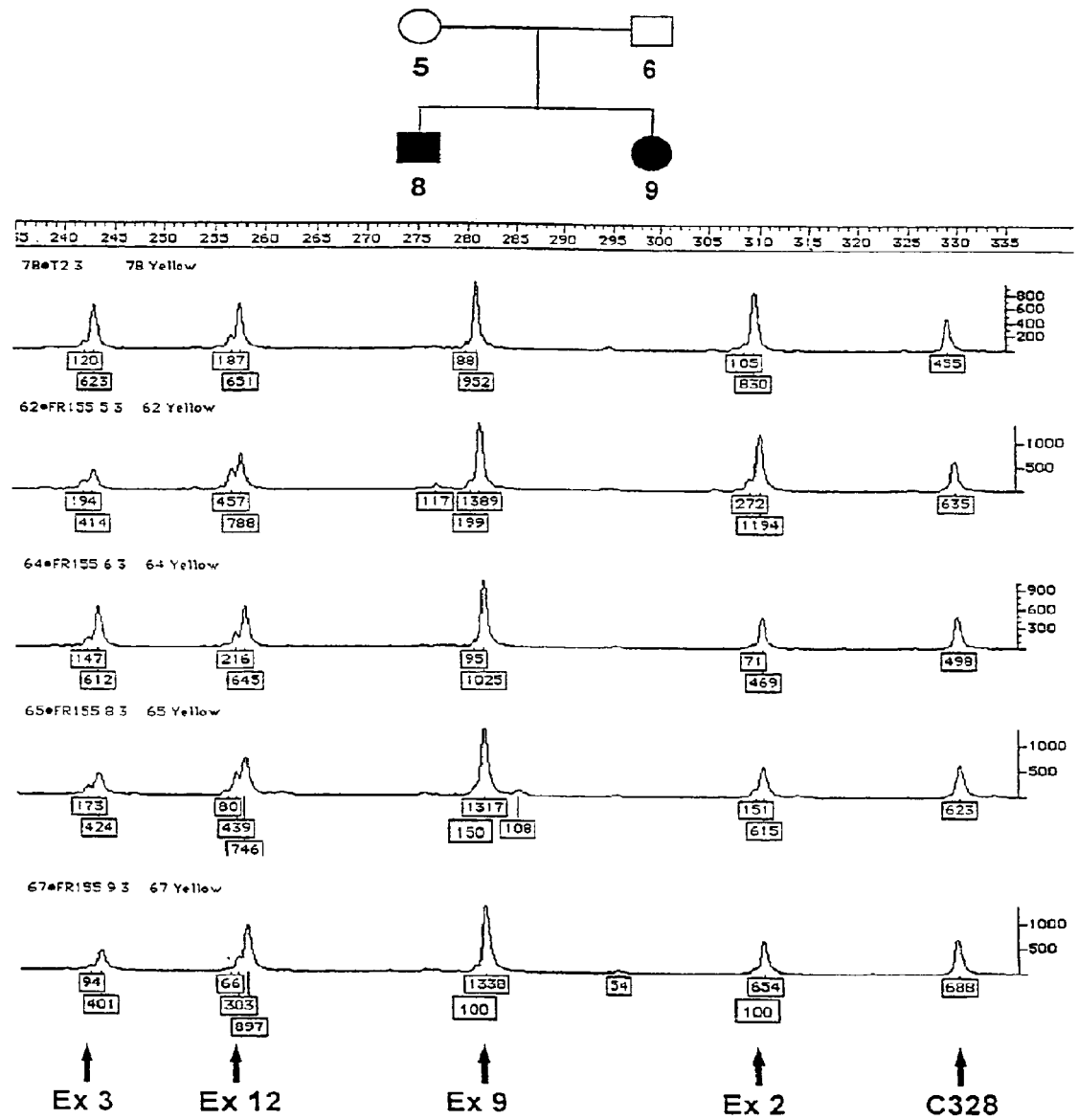

FIG. 4: Results of the detection of deletions of heterozygous exons in a family with early onset parkinsonian syndrome (FPD-GRE-WAG-155) according to the semi-quantitative multiplex PCR method of the invention. The black squares (men) and circles (women) represent the individuals affected.

The peaks represent the exons produced by semi-quantitative multiplex PCR. The encircled figures indicate the height of the peaks. The graduated ruler above the electrophoretograms indicates the size of the PCR products in base pair.

Table 1: Oligonucleotides used for the ASO technique. The nucleotide changes in the sequence of the oligonucleotides are represented in bold and underlined. WT=wild type; V=variant.

Table 2: Summary of the mutations identified. The positions of the nucleotides are given according to the cDNA sequence published in the DNA Data Bank of Japan (DDBJ; accession number AB009973) and are illustrated in FIG. 1. PAGE=polyacrylamide gel electrophoresis; ASO=technique for the detection of mutations using an allele specific oligonucleotide.

Table 3: Clinical characteristics of patients as a function of the type of genetic alteration. The patients of the IT-020 family who are composite heterozygous for a missense mutation and a truncating mutation do not appear in the table. a: p<0.05 for the comparison between the patients with a homozygous deletion and the patients with truncating mutations.

Table 4: Frequency and consequences of the deletions/multiplications of exons del=deletion, het=heterozygote; hom=homozygote Table 5: Ratio of the results obtained in FIG. 4. The height of the peaks is given for each exon in the left hand part of the table, the values for the double peaks having been added. The right hand part of the table provides the calculation of the ratios of the values of the peaks. Italics=normal value; underlined=pathological value compared with the control. In the second line of the table, for each case, the ratio of the control is divided by the ratio of the case. The pathological values are either ≤0.625 or ≥1.6 (=1/0.625). Deletions of exons were detected for the subjects FR 155 5 (exon 3), FR 155 6 (exon 2), FR 155 8 and FR 155 9 (exons 2+3). For the latter two affected subjects the value of the exon 3/2 ratio is normal given that the two exons were heterozygously deleted.

B—Materials and Methods

1. Families and Patients

In a first series of experiments, 38 families were selected according to the following criteria:

parkinsonian syndrome reactive to levodopa, ii) starting age at most 45 years for at least one of the affected members, and iii) transmission compatible with an autosomal-recessive heredity.

In another series of experiments, 77 families were selected according to the following criteria (as indicated in Lücking et al, 1998; Abbas et al, 1999): i) presence of a parkinsonian syndrome with a good response to levodopa (≥30% improvement) in at least two members of a phratry (or only one if there is a notion of consanguinity); ii) absence of exclusion criteria such as Babinski's syndrome, ophthalmoplegia, dementia or dysautonomia occurring before two years of progression; iii) beginning ≤45 years in at least one of those affected; iv) heredity compatible with recessive autosomal transmission (several patients in a single generation with or without a notion of consanguinity). The families were from France (n=20), Italy (n=19), Great Britain (n=14), the Netherlands (n=9), Germany (n=9), Lebanon (n=2), Algeria (n=1), Morocco (n=1), Portugal (n=1), Vietnam (n=1).

Furthermore, 102 isolated cases, with no known consanguinity, were selected with the same clinical criteria. They were from France (n=31), Italy (n=23) and Great Britain (n=26), Germany (n=21)n the Netherlands (n=1).

All the patients were evaluated according to a standard protocol. The informed consent of all the participants was obtained in writing.

2. Analyzis of the Parkin Gene

The DNA of the 12 exons encoding the parkin gene was amplified by PCR from peripheral blood leukocytes, for each index case, according to the conditions described in Kitada et al. Briefly, the amplification was carried out on 100 ng of DNA, in the presence of 350 µM of each dNTP, 350 µM of each primer, and Taq polymerase. The amplification conditions are 35 cycles at 94° C. for 30 sec, at 55-61° C. for 30 sec, and then at 68° C. for 30 sec. For exons 4 and 7, only the pair of intron primers was used. The sequence of the 12 exons was prepared on two strands with the primers used for the PCR amplification, with the sequencing kit "Big Dye Terminator Cycle Sequencing Ready Reaction" (ABI PRISM) and analyzed after electrophoresis on the ABI 377 sequencer with the "sequence analyzis 3.0" software (ABI PRISM).

The detection of the mutations in the samples and the analyzis of a population of 45 control individuals was carried out by three techniques, which may be used alone or in combination(s): PCR/restriction with the appropriate restriction enzyme; ASO technique ("Allele Specific Oligonucleotide"), and polyacrylamide gel electrophoresis ("PAGE") as illustrated in Table 2. More particularly, these techniques were carried out as described below.

The ASO technique: this approach consists in hybridizing two oligonucleotide probes with an amplified sample (for example by PCR), the first specific for and covering a genetic alteration, the second specific for and covering the corresponding wild-type region. Thus, in the presence of a mutated gene, only the first probe allows hybridization with the DNA fragment, whereas in the presence of a nonmutated gene, only the second probe allows hybridization with the DNA fragment. In the case of a heterozygous gene, a hybridization is obtained with each of the probes. This technique may also be carried out concomitantly with the amplification, using two pairs of primers, the first comprising a primer specific for and covering the corresponding wild-type region. In this embodiment, in the presence of a mutated gene, only the first pair allows the amplification of a DNA fragment, whereas in the presence of a nonmutated gene, only the second pair of primers allows the amplification of a DNA fragment. In the case of a heterozygous gene, an amplification product is obtained with each of the pairs of primers.

For carrying out this technique, 10 µl of PCR product were denatured at 95° C. for 5 min, deposited on Hybond N+ nylon membranes (Amersham), and then microwave-fixed at 600 W for 2 min. The specific primers (or oligonucleotides) used for the detection (or, where appropriate, for the amplification), are described in the examples (see Table 1). For exon 3, the exon primers Ex3iFor (forward) and Ex3iRev (back) were used. The sequence of these primers is the following:

```
Ex3iFor:
                                    (SEQ ID No: 6)
5'-AATTGTGACCTGGATCAGC-3'

Ex3iRev:
                                    (SEQ ID No: 7)
5'-CTGGACTTCCAGCTGGTGGTGAG-3'
```

These oligonucleotides (including the primers, in the case of a simultaneous amplification), labeled with dCTP32 by means of the Terminal Transferase Kit (Boehringer Mannheim) were hybridized with the membranes at 44° C. overnight in a buffer consisting of 5×SSC, 5×Denhardts and 0.1% SDS. The membranes were then washed twice for 30 min in a 2×SSC medium at 59° C. and exposed to an MP film (Amersham) for 3-6 hours.

PCR/restriction technique: this technique is based on the use of restriction enzymes whose digestion profile becomes modified because of the genetic alteration. Preferably, this technique therefore uses restriction enzymes whose site is modified (destroyed or created) by the genetic alteration.

Thus, depending on the nucleic acid digestion profile (generally amplification product), it is possible to distinguish the presence or otherwise of the genetic alteration searched for. Of course, this technique is most particularly appropriate for the search for straightforward genetic alterations, causing a modification in an enzymatic cleavage site. For its use, 15 µl of amplification product is digested in the presence of appropriate restriction enzyme(s), according to the manufacturer's recommendations. The particular enzymes used in the examples and the expected size of the restriction fragments are given in Table 2.

Polyacrylamide gel electrophoresis ("PAGE") technique: this technique makes it possible to detect the presence of mutations by measuring the size of the amplification products. It is therefore most particularly appropriate for the detection of genetic alterations of the insertion or deletion type. For its use, a labeled forward primer (5'-fluorescent, Hex) was used to amplify exon 2 of the parkin gene. The presence of the 202-203delAG alteration, resulting in a shorter PCR product (306 vs 308 bp) was established by measuring the size of the amplified fragment using an ABI377 automated sequencer equipped with "Genescan 2.0.2" and "Genotyper 1.1.1" software (ABI PRISM).

The numbering of the nucleotides used in the present application is given with reference to the sequence of the cDNA which exists in the DNA Data Bank of Japan (DDBJ; accession number: AB009973). The sequence is represented in FIG. 1. This sequence differs from the sequence described by Kitada et al. at the level of nucleotide 768. The sequence presented in FIG. 1 corresponds to the wild-type protein found in European populations.

3. Semi-quantitative Multiplex PCR for the Detection of Deletions/Multiplications of Exons in the Homozygous and Heterozygous State a) Principles The detection of heterozygous deletions or multiplications of exons in the Parkin gene cannot be carried out by nonquantitative PCR. Thus, a semi-quantitative PCR which compares the relative amount of template DNA is sufficient to know if 50% of the template DNA is missing for one or more exons or, on the contrary in the case of a heterozygous or homozygous multiplication, if there is for example 50% (heterozygous duplication), 100% (homozygous duplication or heterozygous triplication) or 200% (homozygous triplication) of DNA in excess for one or more exons. To carry out this comparison, several exons from the same individual are simultaneously amplified, in a PCR reaction (multiplex PCR), the coamplified exons serving as internal standard for quantity. The PCR is carried out with fluorescent primers, such that the quantity of PCR product can be measured by the height of peaks on an automated sequencer (ABI Prism 377), as applied for example in the Applied Biosystems LOH (Loss of Heterozygosity) Assay. The quantity of PCR product (height of the peak) is directly linked to the quantity of template DNA as long as the PCR is in its exponential phase which means an absence of limitation by the available substrates. Each multiplex PCR, for a given combination of exons, produces a typical peak height distribution for a control individual as well as defined ratios between the different peaks.

A homozygous deletion of an exon will be demonstrated by the absence of the corresponding peak. If an exon is deleted in the heterozygous state, the corresponding peak will have half of its normal height, which will change the ratio between the deleted and nondeleted exons by a factor of 2 compared with a control (comparing the high value with the low value; FIG. 4 and Table 4 relating to FIG. 4). For the duplications of exons, the ratios change by a factor of 1.5 for the heterozygotes and by a factor of 2 for the homozygotes (still by comparing the high value with the low value). Thus, the factors for a heterozygous or homozygous triplication are 2 or 3, respectively (still by comparing the high value with the low value). In order to be able to also detect a deletion or a multiplication of the entire Parkin gene, a PCR product of 328 base pairs (C328) of a gene situated at a distance (gene for Transthyretin) is amplified and serves as external standard in one of the multiplex PCRs. The fact that only the ratios of the heights between the peaks are compared renders, by first approximation, the method independent of the quantity and of the quality of the DNA.

b) Establishment of the Appropriate Conditions for Multiplex PCR

During preliminary experiments, it was noted that the exons which exhibit the best amplification could negatively influence the amplification of other exons, for which the efficiency was not as good. Thus, the exons whose amplification efficiency was comparable were grouped together. Furthermore, as the size of the PCR product can influence the amplification yield (the short sequences being as a rule better amplified than the long sequences), the PCR products of comparable size were grouped together in the multiplex reaction. Thus, three combinations of exons were chosen:

Comb 1: Ex 4o (261 bp)+7o (239 bp)+8 (206 bp)+11 (303 bp),

Comb 2: Ex 5 (227 bp)+6 (268 bp)+8 (206 bp)+10 (165 bp) and

Comb 3: Ex 2 (308 bp)+3i (243 bp)+9 (278 bp)+12 (255 bp)+C328

(external control of 328 base pairs).

The primers used are those described by

Kitada et al (1998). For exon 3, a pair of exonic primers was used:

```
For:
                                    (SEQ ID No: 8)
5'-(Hex)AATTGTGACCTGGATCAGC-3'
and Rev:
                                    (SEQ ID No: 9)
5'-CTGGACTTCCAGCTGGTGGTGAG-3'.

The primers for C328 being:
TTRForHex:
                                    (SEQ ID No: 10)
5'-(Hex)ACGTTCCTGATAATGGGATC-3'
and TTR328Rev:
                                    (SEQ ID No: 11)
5'-CCTCTCTCTACCAAGTGAGG-3'.
```

In order to obtain peaks of comparable heights in each multiplex PCR and to be situated in the exponential phase for each exon, the PCR conditions were adjusted permanently (by partly following the recommendations of Henegariu et al (Henegariu et al, 1997). In particular, the hybridization and extension temperatures were reduced and the concentration of $MgCl_2$ and the duration of the extension were increased. Furthermore, the concentrations of primers were adjusted from a standard concentration of 0.8 µM, according to the amplification efficiency (the concentrations of primers being reduced for the exons which amplify well, and increased for the others).

Each combination of exons was tested in order to verify that the exponential phase was established, this being in two multiplex PCRs in parallel for the 3 combinations of primers, on a control individual with 22, 23 and 24 cycles. The peak heights were corrected for the variations in loadings according to the internal molecular weight marker (Applied Biosystems TAMRA 500 XL). The corrected peak heights were compared to the number of cycles, and represent, on a logarithmic scale, an ascending straight line which demonstrates that the exponential phase was established for the following conditions:

5 minutes at 95° C. for one cycle,
30 seconds at 95° C., 45 seconds at 53° C. and 2.5 minutes at 68° C. for 23 cycles,
5 minutes at 68° C. for one cycle.

The reaction was carried out with 40 ng of DNA in a volume of 25 µl of PCR solution, with 3 mM MgCl$_2$, 0.2 mM dNTP and 1 U Taq/25 µl. The concentration of each primer was:

Ex 2 (0.8 µM), Ex 3 (0.4 µM), Ex 4 (1.0 µM), Ex 5 (0.6 µM), Ex 6 (1.4 µM), Ex 7 (0.44 µM), Ex 8 (in comb 1:1.0 µM and in comb 2:0.8 µM), Ex 9 (0.4 µM), Ex 10 (1.04 µM), Ex 11 (0.8 µM), Ex 12 (1.2 µM) and C328 (1.92 µm).

c) Applications of Multiplex PCR, Internal Controls and Electrophoresis

As a general rule, the multiplex PCRs were carried out at least in two parallel reactions for each individual. For each series of patient, at least one positive control (with a heterozygous deletion of known exons) and one negative control (control individual) were treated in parallel in order to obtain the normal and pathological values for each reaction premix, so as to avoid erroneous results due to possible differences in the premix (variation of pipetting). Two additional controls were added, which did not contain template DNA. 1.5 to 2.5 µl of the PCR product were mixed with 4 µl of loading buffer (comprising 0.3 µl of the Applied Biosystems TAMRA 500 XL size marker). 1.5 µl of this mixture was loaded onto a 4% denatured polyacrylamide gel containing 96 wells on an ABI 377 automated sequencer. The gels are analyzed by the GeneScan 3.1 and Genotyper 1.1.1 software packages (Applied Biosystems). The peak heights are measured as indicated in Genotyper. For the double peaks with one base pair difference (caused by the fact that Taq polymerase inconstantly adds an A to each end), the two peak heights are added. The ratios of each combination of peaks are calculated for each reaction, using the Excel 5.0 software (Table 5) and the mean values are calculated for two reactions.

d) Interpretation

For the deletions, the results are interpreted as pathological if the difference in ratio was a factor of at least 1.6 or ≤0.625 (=1/1.6) in all the respective ratios between the control and the case (ratio of the subject/ratio of the control—Table 5 relating to FIG. 4). When the differences in ratios between the parallel reactions are contradictory (for example because of a weak amplification in one of the PCRs), the ratios obtained with a satisfactory amplification are taken into account on condition that they are normal.

For the duplications, a change in the ratios by a factor of 1.30-1.65 or >1.75 is interpreted as a heterozygous or homozygous duplication respectively (by comparing the high value with the low value).

For a triplication, a change in the ratios by a factor of 1.6-2.4 or >2.6 is interpreted as a heterozygous or homozygous triplication respectively (by comparing the high value with the low value).

However, as the conditions were continuously adjusted during the development of the method, some of the results were obtained under slightly different conditions. These results are taken into account when they are clearly normal or pathological and reproducible. In ambiguous situations, the experiment was repeated under appropriate conditions.

4. Analyzis of Cosegregation and of a Control Population a) Point Mutations

The variants of the Parkin sequence were tested for their cosegregation in the families (according to the availability of other samples) and for their presence in a population of controls without Parkinsonian syndrome (61 to 73 individuals). Because of the certainly pathogenic character of the 1142-1143delGA mutation, controls were not tested for this mutation. The techniques used are PCR and digestion with the appropriate restriction enzyme or polyacrylamide gel electrophoresis (PAGE) (see Table 2). When the variant did not cause any change in restriction site by itself, a site was artificially created with the aid of a primer with a mismatch. The primers were designed so as to introduce the change of base near the position of the sequence variant, so as to create a restriction site which includes this variant. The primers are indicated in the table below.

Modified primers (not complementary to the wild-type sequence for one base) for PCR:

| Mutation | Restriction enzyme | Primer F | Primer R |
|---|---|---|---|
| Asp280Asn | AlwI | Ex 70 For | 5'-GGCAGGGAGTAGCCAA GTTGAGGAT-3' (SEQ ID NO. 12) wild-type sequence G |
| Arg334Cys | BstUI | Ex 9 For | 5'-AGCCCCGCTCCACA GCCAGCGC-3' (SEQ ID NO. 13) wild-type sequence |

The change in base pair introduced is underlined by comparison with the wild-type sequence.

b) Deletions or Multiplications of Homozygous or Heterozygous Exons

The cosegregation of a deletion or of a multiplication of exons in the families was analyzed with the aid of the methods described above. A control population was not tested because of the highly probable pathogenic character of the mutations, which causes an internal deletion of the protein, with or without a reading frame shift.

5. Linkage Analyzis

To test the linkage to the PARK2 locus, four microsatellite-type markers, situated near the locus, were tested (D6S1579, D6S411, D6S1550 and D6S305) as described by Tassin et al (1998).

C—Results a) In a First Series of Experiments, the Analyzis of the Parkin Gene was Carried Out in the Index Case of 38 Families with AR-JP which Contain 87 Patients.

1. Detection of Deletions of Exons

The amplification of the exons revealed the presence of a deletion in the homozygous state in three families: deletion of exon 3 in a French family (SAL-024) and a Portuguese family (SAL-711), and of exons 8 and 9 in an Algerian family (DEL-001). These deletions are transmitted with the disease because they are detected in each family in the homozygous state in all patients but not in the healthy related ones sampled (FIG. 2).

2. Detection of Point Mutations

The sequence analyzis in the families without homozygous deletion revealed the presence of 16 variants of the nucleic sequence: 12 in the exons and 4 in the introns (Tables 2 and 3, FIG. 3). Three variants cause a reading frame shift and the synthesis of a truncated protein. They are mutations 202-203delAG (Gln34Arg(Stop37)) and 225delA (Asn52Met(Stop81)) in exon 2 and 321-322insGT (Trp74Cys(Stop81)) in exon 3 which are found respectively in the families IT-020 and UK-086, TOU-096, LYO-119. These mutations, with the exception of 202-203delAG are in the homozygous state. A nonsense mutation 1459G>A (Trp453Stop) in exon 12 is present in the homozygous state in the IT-006 family. Eight of the variants are of the missense type. In exon 4, 584A>T (Lys161Asp) and 601G>A (Ser167Asn) are in the heterozygous state in patients of the IT-020 and SAL-730 families, respectively. In exon 7, the variants 867C>T (Arg256Cys) and 924C>T (Arg275Trp) are found in the heterozygous state in the DE-012 and IT-015 families, respectively. In exon 10, the variant 1239G>C (Val380Leu) is found in the heterozygous and homozygous state in 11 families (IT-014, IT-020, IT-058, SAL-017, GRE-029, SAL-038, TOU-096, SAL-431, UK-006, UK-086, DE-022). In exon 11, the variant 1281G>A (Asp394Asn) is detected in the heterozygous state in the UK-046 family and 1345C>A (Thr415Asn) in the homozygous state in the IT-014 family. Finally, the variant 768C>T (Pro223Ser) is not pathogenic, because it is detected in the homozygous state in all the individuals sequenced, suggesting that it is a typographical error in the parkin sequence [Kitada et al., 1998]. The search for these variants in the control population reveals that three of them represent polymorphisms (Table 2): Ser167Asn, Val380Leu and Asp394Asn. The other variants most probably constitute causal mutations because they cause the synthesis of truncated parkin or nonconservative substitutions or substitutions affecting one of the amino acids capable of being phosphorylated. Furthermore, they segregate with the disease in the families and are not detected in 90 control chromosomes.

The variants identified in introns 2, 3, 6 and 7 (IVS2+25T>C (272+25T>C), IVS3-20C>T (514-200>T), IVS6+19T>C (835+19T>C) and IVS7-35A>G (973-35A>G)) constitute polymorphisms (Table 2). They are not located near splicing sites and are detected in the control chromosomes.

3. Functional Domains of Parkin

A study of the functional domains of parkin was undertaken by analyzis and comparison of sequences. This study shows that the conservative change in amino acid Thr415Asn is located in the consensus sequence of a cAMP- and cGMP-dependent protein kinase (KKTT) and in the phosphorylation site of a protein kinase C (TTK). This study shows, in addition, that the nonsense mutation Trp453Stop is located in an N-terminal myristoylation site (GCEWNR).

4. Phenotype Genotype Correlations

The homozygous deletions and the point mutations were detected in 12 families which contain 26 patients. The average age at onset is 36.7 years with extremes of 7 to 56 years (Table 3). The comparison between the families according to the functional consequences of the mutations (homozygous deletion, truncating mutation and missense mutation) does not reveal any significant difference in the age at onset, in the severity or the frequency of the associated signs, except for tremor which is significantly less frequent in families with a homozygous deletion, compared with families with truncating mutations (Table 3).

b) Detection of New Point Mutations

Eight new point mutations in exons were identified, of which six are missense mutations one truncating and one nonsense: 734A>T (Lys211Asn) in exon 6, 905T>A (Cys268Stop), 939G>A (Asp280Asn) and 966T>G (Cys289Gly) in exon 7, 1084G>A (Gly328Glu), 1142-1143delGA and 1101C>T (Arg334Cys) in exon 9 and 1390G>A (Gly430Asp) in exon 12. Five of the missense mutations lead to nonconservative amino acid changes and one to a conservative change (Cys289Gly). Furthermore, a deletion of five base pairs in intron 8, located at positions −21 to −17 relative to exon 9 was detected. All these sequence variants were not detected in 61 to 73 control individuals (the 1142-1143delGA mutation was not tested) and do not therefore represent polymorphisms. The results are detailed in Table 2.

c) Detection of New Homozygous Deletions of Exons

Homozygous deletions of exons were detected in 3 families in addition to the deletions previously reported by Hattori et al (1998a) and Lucking et al (1998) for exon 3 and by Hattori et al (1998a) for exons 3+4. These deletions relate to exons 3 (FDP-ANG-GEO-141), 3+4 (IT-064) and 5+6 (SPD-LIB-HAG-076). The consequences of the deletions of exons on the reading frame and their relative frequency in the sample are indicated in Table 4.

d) Detection of Homozygous and Heterozygous Duplications/Triplications

Five new types of duplications of exons were detected: a duplication of exon 3 in the homozygous state (SPD-NIC-AIT-091) and a duplication of exon 3 in the heterozygous state (SAL 399 213). In addition, heterozygous duplications of exon 6 (FPD-LIL-CHA-171), of exon 7 (DE 4001) and of exon 11 (SAL 399 213) were detected. Two types of triplication were detected: a triplication of exon 2 in the homozygous state (RM 347) and a the heterozygous state (RM 330).

e) Detection of New Heterozygous Deletions

Thirteen different combinations of heterozygous deletions of exons were detected in 21 families. The following deletions were observed: exons 2, 2+3, 2+3+4, 3, 3+4, 3–6, 3–9, 4, 5, 6, 6+7, 7+8+9 and 8. The deletions of exons 2, 2+3, 2+3+4, 3–6, 3–9, 6, 6+7, 7+8+9 and 8 are new.

For two families (Sal-Hab-436 and UK 12416), it was not possible to establish with certainty if the heterozygous mutations of exons 2+3 or 6–7, respectively, were situated on the same chromosome or if they were composite heterozygous cases because of the absence of DNA for other members of these families. The consequences of the deletions and of the multiplications of exons described on the reading frame and their relative frequency in our sample are indicated in Table 4.

f) Recurring Point Mutations

Five point mutations were detected in more than one family. These mutations are 202-203delAG (in the heterozygous or homozygous state in 5 families), 255delA (in the homozygous or heterozygous state in 6 families), Lys211Asn (in the heterozygous state in 2 families), and Arg275Trp (in the heterozygous state in 5 families).

g) Frequencies of the Different Types of Mutations and of the Composite Heterozygotes Among the families with Parkin mutations, homozygous deletions of exons were detected in 8 families, point mutations in the homozygous state in 10 families, a duplication of homozygous exon in one family and a triplication of exon in one family. The patients from 21 families were composite heterozygotes for two different mutations (3 times for the different point mutations, 6 times for a point mutation and an exon deletion, twice for a point mutation and a duplication, once for a triplication and an exon deletion, once for two different duplications of exon and 6 times for two different deletions of exons; see example FIG. 4). In two cases, it was not possible to determine if heterozygotes with deletions of several composite adjacent exons were involved, and in 13 cases, only one mutation in the heterozygous state (6 point mutations and 7 exon mutations) was detected.

D—Discussion

The present invention relates to variants of the Parkin gene, their diagnostic and/or therapeutic use, as well as techniques for the detection of alterations (in particular of deletions of heterozygous exons and of multiplications of exons) of the Parkin gene.

The detection of different causal genetic alterations (in particular of homozygous deletions, point mutations, insertions and multiplications of exons) demonstrate that the abnormalities in the parkin gene constitute a frequent cause of AR-JP.

1. First Study On 38 European Families

A first study made it possible to demonstrate the existence of deletions, mutations and insertions in the parkin gene.

The pathogenic role of the homozygous deletions appears to be easy to establish. In the 2 mutations described, deletions of exon 3 and of exons 8-9, the loss of the exon is accompanied by a reading frame shift leading to the appearance of a premature stop codon. In the absence of alternative splicing, a truncated protein results therefrom.

Eight of the exon variants constitute causal mutations. First, these mutations segregate with the disease in the families. Secondly, these variants are not detected by ASO, PAGE or PCR/restriction in 90 control chromosomes. Thirdly, the functional consequences of the mutations appear to be deleterious. It is easy to understand that the 4 truncating point mutations (Gln34Arg(Stop37), Asn52Met (Stop81), Trp74Cys(Stop81), Trp453Stop) detected in the homozygous state in the patients of 3 of the 5 families will cause a loss in the parkin function in accordance with the autosomal-recessive transmission of the disease. Three of the four missense mutations cause nonconservative changes in amino acids. One of them (Lys161Asp) is associated with a truncating mutation on the other allele which reinforces the assumption of a pathogenic role. A missense mutation is conservative (Thr415Asn), but affects a potential phosphorylation site. Three of the missense mutations are present in the heterozygous state in patients whose other mutation has not been characterized. It is probable that deletions of one or more exons in the heterozygous state are involved which cannot be visualized with the techniques used for this study.

The abnormalities detected in the parkin gene are varied and there are no hot spot mutations. It should be noted that the truncating point mutations preferably correspond to the N- and C-terminal regions of parkin (comprising in particular the ubiquitin-like and ring "RING-finger" units, respectively) whereas the missense-type mutations affect the central region. Only two of the 11 mutations described in this first study are found in several families. The homozygous deletion of exon 3 is detected in the French SAL-024 and Portuguese SAL-711 families. The mutation with a reading frame shift 202-203delAG (Gln34Arg(Stop37)) is visualized in the heterozygous state in the Italian IT-020 and English UK-086 families. The different 2.0 origin of the families is in favor of the hypothesis for the independent occurrence of these mutations.

The mutations described affect families from 6 countries: Algeria, Germany, England, France, Italy and Portugal. The study of the phenotype in the families with a mutation shows that the clinical spectrum associated with the abnormalities of parkin is broader than in the Japanese families [Kitada et al., 1998]. These results confirm the observations made in the European and North African families studied by genetic linkage [Tassin et al., 1998]. The age of onset is above 50 in several patients, ranging up to 56. Certain clinical signs such as dystonia or pyramidal signs in the lower limbs are not always present in the carriers of mutation even after periods of evolution of several decades. Overall, the phenotype remains very similar between the groups of patients classified according to the functional consequences of the mutations. However, the presence of painful dystonia episodes appears to be encountered exclusively in patients carrying homozygous deletions. The absence of a significant difference for the age of onset, the severity and the frequency of the associated signs between the truncating point mutations and the missense mutations suggests that the modified amino acids in the latter play an important role in the physiology of parkin.

In conclusion, this first study underlines the frequency of the mutations in the parkin gene in early-onset familial parkinsonian syndromes in Europe. Abnormalities in this gene are also responsible for more tardive or atypical parkinsonian syndromes. The role of mutations of parkin or of its polymorphisms in the isolated cases remains to be determined. The mutations detected are very diverse both by their nature and by their location. The study of their location in parkin suggests that many regions of the protein contribute to its as yet unknown function.

2. Method for the Detection of Deletions of Exons and Multiplications of Exons

For the first time, the detection of deletions of exons in the heterozygous state and of multiplications of exons (for example duplication, triplication) in the homozygous and heterozygous state in the Parkin gene is described. This aspect is advantageous because exon deletions are relatively frequent (see later). As a method of detection, a semiquantitative multiplex PCR protocol was chosen and developed. This method had previously been validated for gene assay, for example for the detection of deletions of the PMP22 gene (Poropat and Nicholson, 1998), provided that the PCR amplification is in the exponential phase. In all these experiments, the choice of coamplified controls which serve as a standard for the quantification is critical (Prior, 1998). In the experiment, the nondeleted exons serve as internal controls in the multiplex PCR amplification in the same individual. Combinations of 4 or 5 exons were chosen so as not to contain more than 2 adjacent exons, because such exons cannot serve as controls in the case of a deletion of the two. The exon on a different gene (Transthyretin) was coamplified in one of the three combinations in order to identify heterozygous deletions of the entire Parkin gene. This external control was indirectly represented in the other two combinations, which include exons on either side of exon 9; the latter being tested with Transthyretin.

The results obtained by this method were very reproducible and the abnormal results show differences in the ratios of a factor, which corresponds to that expected in theory. These results show that this is a simple and validated method for rapid screening.

Furthermore, small deletions or insertions in the PCR product, which are relatively frequent (see below) may be simultaneously detected by this method.

3. Deletions Of Exons And Multiplications Of Exons

It was possible to identify four duplications of exons and one triplication of exons which had never been described in the Parkin gene before, but whose relative frequency is low. Furthermore, 10 combinations of new deletions of exons were identified with, for the first time, the demonstration of the deletions which carry exon 2. The relative frequency of the point mutations and of the deletions of exons was estimated at about 50%. Thus, the deletions of exons (heterozygous or homozygous) may represent up to 50% of the Parkin mutations, emphasizing the importance of the technique described here. In fact, this technique has made it possible to detect mutations in 26 of the 53 families. Thus, in the sample studied, the point mutations and the deletions in the Parkin gene have the same frequency, whereas the deletions of exons are predominant in the Japanese population (Hattori et al, 1998). The functional consequences of the deletions or of the multiplications of exons described (reading frame shift or deletion/multiplication in phase) were deduced from the published cDNA sequences for Parkin (Kitada et al, 1998) and are speculative, because the absence of a PCR product does not indicate that there is necessarily a deletion of the exon in its entirety (see above). However, the pathological role of the modifications detected is highly probable, because they are transmitted with the disease in the families which have been able to be tested, they are associated with point mutations in composite heterozygotes and the deletions are identified with a frequency similar to that of point mutations. Likewise; in the isolated cases, the frequency of the heterozygous deletions and of the point mutations is similar. In the case of exon 3, exonic primers were used, which demonstrate the alteration of this exon when there is no PCR product. Furthermore, in some of the cases, several juxtaposed exons were simultaneously deleted, which is an argument for a large genomic deletion.

Heterozygous deletions or multiplications of the entire Parkin gene were not observed. This is probably a rare event given the very large size (about 500 kb) of this gene (Kitada et al, 1998).

The exon deletions observed frequently effect exons 3 to 5. This observation has been confirmed in European families. Furthermore, it has been demonstrated that exon 2 alone or associated with others is also frequently involved in European families (Table 2).

4. New Point Mutations

The identification of 8 new point mutations (6 of the missense type, 1 truncating and 1 of the nonsense type) increases the diversity of the point mutations in the Parkin gene. The mutations described are pathogenic, as the segregation with the disease has shown, and are not detected in 122 to 147 control chromosomes (mutation 1142-1143delGA not included). Even if the Cys289Gly change is conservative, this change in amino acid may have substantial deleterious consequences, if the cysteine at position 289 is involved in a disulphide bridge, which is important for the function of the protein.

Interestingly, 2 patients of the UK-040 family exhibit 3 different mutations (see Table 5): one Arg334Cys missense mutation in exon 9 in the homozygous state, one homozygous deletion of 5 base pairs at position −17 to −21 of intron 8, and one nonconservative Asp280Asn missense mutation in the heterozygous state. It may be suspected that the Arg334Cys mutation in the homozygous state is causal, but the deletion of five base pairs in the homozygous state, near the acceptor splicing site of exon 9, could also have functional consequences.

Five point mutations are present in several families analyzed. The three most frequent are 255delA (detected in 6 families) and 202-203delAG (found in 5 families) and Arg275Trp (detected in 5 families). A foundation effect could be suspected for the 255delA mutation which affects 5 French families. However, this hypothesis can only be verified by analyzis of the haplotypes.

5. Epidemiological Genetics

The results obtained show that 34 of the 77 families with an early-onset parkinsonian syndrome exhibit mutations of the Parkin gene, emphasizing the importance of this gene in European families. The detection of mutations in 18 of the 102 cases isolated and analyzed is more difficult to interpret because the number is smaller and the analyzis of some cases is not complete. However, it is striking to note that the age at onset of the 7 cases for which it is known is particularly early (13 to 22 years) and that there are very few cases with very early onset without mutation in the Parkin gene (for example IT-NA-JMP-3). This result suggests that the frequency of the mutations of the Parkin gene in isolated cases increases when their age decreases, especially before the age of 25. The observation of mutations in the Parkin gene in isolated cases is not surprising if it is considered that in small families, an autosomal recessive disease has every chance of appearing as an isolated case. Analyzing a larger sample will be useful for determining precisely the frequency of the Parkin mutations in the isolated cases, according to the age at onset.

Mutations were identified in families from a wide variety of origins: France, Italy, Great Britain, Germany, The Netherlands, Algeria, Portugal. These results show that the mutations in the Parkin gene are detected in all the populations tested so far.

6. Patients with an Abnormality in the Parkin Gene in the Heterozygous State

Although the technique for the detection of heterozygous deletions of exons or of multiplications of exons allowed us to identify composite heterozygous cases, in about ¼ of the families (13 out of 53), a single mutation was detected. This includes 6 cases with a point mutation in the heterozygous state and 7 with an exon deletion in the heterozygous state. The pathogenic role of these mutations is highly probable because they cause a nonconservative change in amino acid or a truncated protein. Furthermore, one of these mutations of the missense type (Arg275Trp) is associated with another heterozygous point mutation (Gly430Asp) and with heterozygous exon deletions (exon 3–6 or exon 5+6), carried by the other allele in three different families. The absence of detection of a mutation on the other allele in 13 families suggests that a second undetected mutation affects another region of the gene. This hypothesis is strengthened by the fact that in 6 families probably linked to the PARK2 locus, because the patients are haploidentical for 4 markers for the region, no mutation was detected. Thus, other regions of the gene could be affected, such as the promoter regions, the untranslated 5' and 3' regions, or intron sequences.

7. Genetic Heterogeneity of the Early Onset Autosomal Recessive Parkinsonian Syndromes In 5 of the 77 families, it has been possible to exclude a genetic linkage at the Parkin locus. Furthermore, no mutation was identified in 21 families for which this locus could not be conclusively excluded. These results suggest that there may be at least one other locus for families with an early onset autosomal recessive parkinsonian syndrome in Europe. This hypothesis had been proposed by Leroy et al (1998), which reports a family with two branches, of which one exhibits deletions of the Parkin gene, whereas the other does not exhibit either these deletions or the same haplotype, which excludes a linkage to this locus.

8. Conclusions

A novel method for the detection of heterozygous deletions of exons or multiplications of exons is reported. In particular, the duplications/triplications of exons and deletions of exon 2 and of other combinations of exons are novel. In combination with the sequencing of exons, it has been possible to identify eight novel point mutations and an intron deletion which could affect a splicing site. Thus, 34 of the 77 families analyzed (about 50%) exhibit mutations in the Parkin gene. Furthermore, the mutations in this gene were detected in 19 isolated cases. In the European population, the proportion of point mutations and deletions of exons appear to be identical. Two mutation hot points which correspond to deletions at exons 3 to 5 and to three point mutations (202-203delAG, 255delA and Arg275Trp) were in addition detected.

BIBLIOGRAPHIC REFERENCES

Abbas N, Lücking C B, Ricard S, Dürr A, Bonifati V, De Michele G, Bouley S, Vaughan J R, Gasser T, Marconi R, Broussolle E, Brefel-Courbon C, Harhangi B S, Oostra B A, Fabrizio E, Böhme G A, Pradier L, Wood N W, Filla A, Meco G, Denefle P, Agid Y, Brice A, The French Parkinson's Disease Genetics Study Group and The European Consortium on Genetic Susceptibility in Parkinson's Disease. A wide variety of mutations in the parkin gene are responsible for autosomal recessive parkinsonism in Europe. *Hum Mol Genet* (1999), 8: 567-574 de Rijk M C, Tzourio C, Breteler M M, Dartigues J F, Amaducci L, Lopez-Pousa S, Manubens-Bertran J M, Alperovitch A and Rocca W A. Prevalence of parkinsonism and Parkinson's disease in Europe: the EUROPARKINSON Collaborative Study. European Community Concerted Action on the Epidemiology of Parkinson's disease. *J. Neurol Neurosurg Psychiatry* (1997j, 62: 10-5

Gasser T, Mÿller-Myhsok B, Wszolek Z K, Oehlmann R, Caine D B, Bonifati V, Bereznai B, Fabrizio E, Vieregge P and Horstmann R D. A susceptibility locus for Parkinson's disease maps to chromosome 2p13. *Nature Genetics* (1998), Hattori N, Kitada T, Matsumine H, Asakawa S, Yamamura Y, Yoshino H, Kobayashi T, Yokochi M, Wang M, Yoritaka A, Kondo T, Kuzuhara S, Nakamura S, Shimizu N and Mizuno Y. *Molecular genetic analyzis of a novel Parkin gene in Japanese families with autosomal recessive juvenile parkinsonism: evidence for variable homozygous deletions in the Parkin gene in affected individuals. Ann Neurol* (1998a), 44: 935-41

Hattori N, Matsumine H, Asakawa S, Kitada T, Yoshino H, Elibol B, Brookes A J, Yamamura Y, Kobayashi T, Wang M, Yoritaka A, Minoshima S, Shimizu N and Mizuno Y. Point mutations (Thr240Arg and Gln311Stop) [correction of Thr240Arg and Ala311Stop] in the Parkin gene [published erratum appears in Biochem Biophys Res Commun 1998 October 20; 251(2): 666]. *Biochem Biophys Res Commun* (1998b), 249: 754-8

Henegariu O, Heerema N A, Dlouhy S R, Vance G H and Vogt P H. *Multiplex PCR: Critical Parameters and Step-by-Step Protocol. BioTechniques* (1997), 23: 504-511

Ishikawa A and Tsuji S. Clinical analyzis of 17 patients in 12 Japanese families with autosomal-recessive type juvenile parkinsonism. *Neurology* (1996), 47: 160-6

Jones A C, Yamamura Y, Almasy L, Bohlega S, Elibol B, Hubble J, Kuzuhara S, Uchida M, Yanagi T, Weeks D E and Nygaard T G. Autosomal Recessive Juvenile Parkinsonism Maps to 6q25.2-q27 in Four Ethnic Groups: Detailed Genetic Mapping of the Linked Region. *Am J Hum Genet* (1998), 63: 80-7

Kitada T, Asakawa S, Hattori N, Matsumine H, Yamamura Y, Minoshima S, Yokochi M, Mizuno Y and Shimizu N. Mutations in the parkin gene cause autosomal recessive juvenile parkinsonism. *Nature* (1998), 392: 605-8

Krÿger R, Kuhn W, Mÿller T, Woitalla D, Graeber M, Kšsel S, Przuntek H, Epplen J T, Schšls L and Riess O. Ala30Pro mutation in the gene encoding alpha-synuclein in Parkinson's disease. *Nature Genetics* (1998), 18: 106-108

Leroy E, Anastasopoulos D, Konitsiotis S, Lavedan C and Polymeropoulos M H. Deletions in the Parkin gene and genetic heterogeneity in a Greek family with early onset Parkinson's disease. *Hum Genet* (1998), 103: 424-7

Lücking C B, Abbas N, Dürr A, Bonifati V, Bonnet A M, de Broucker T, De Michele G, Wood N W, Agid Y, Brice A, The European Consortium on Genetic Susceptibility in Parkinson's Disease and The French Parkinson's Disease Genetics Study Group. *Homozygous deletions in parkin gene in European and North African families with autosomal recessive juvenile parkinsonism. Lancet* (1998), 352: 1355-1356

Matsumine H, Saito M, Shimoda Matsubayashi S, Tanaka H, Ishikawa A., Nakagawa Hattori Y, Yokochi M, Kobayashi T, Igarashi S, Takano H, Sanpei K, Koike R, Mori H, Kondo T, Mizutani Y, Schaffer A A, Yamamura Y, Nakamura S, Kuzuhara S, Tsuji S and Mizuno Y. Localization of a gene for an autosomal recessive form of juvenile Parkinsonism to chromosome 6q25.2-27. *Am J Hum Genet* (1997), 60: 588-596

Polymeropoulos M H, Lavedan C, Leroy E, Ide S E, Dehejia A, Dutra A, Pike B, Root H, Rubenstein J, Boyer R, Stenroos E S, Chandrasekharappa S, Athanassiadou A, Papapetropoulos T, Johnson W G, Lazzarini A M, Duvoisin R C, Di Iorio G, Golbe L I and Nussbaum R L. Mutation in the alpha-Synuclein Gene Identified in Families with Parkinson's Disease. *Science* (1997), 276: 2045-2047

Poropat R A and Nicholson G A. *Determination of gene dosage at the PMP22 and androgen receptor loci by quantitative PCR. Clinical Chemistry* (1998), 44: 724-730

Prior T W. *Determining Gene Dosage (editorial). Clinical Chemistry* (1998), 44: 703-704.

Sunada Y, Saito F, Matsumura K and Shimizu T. *Differential expression of the parkin gene in the human brain and peripheral leukocytes. Neurosci Lett* (1998), 254: 180-182

Takahashi H, Ohama E, Suzuki S, Horikawa Y, Ishikawa A, Morita T, Tsuji S and Ikuta F. Familial juvenile parkinsonism: clinical and pathologic study in a family. *Neurology* (1994), 44: 437-41

Tassin J, Dÿrr A, de Broucker T, Abbas N, Bonifati V, De Michele G, Bonnet A M, Broussolle E, Pollak P, Vidailhet M, De Mari M, Marconi R, Medjbeur S, Filla A, Meco G, Agid Y and Brice A. Chromosome 6-Linked Autosomal Recessive Early-Onset Parkinsonism: Linkage in European and Algerian Families, Extension of the Clinical Spectrum, and Evidence of a Small Homozygous Deletion in One Family. *Am J Hum Genet* (1998), 63: 88-94

Wood N. Genes and parkinsonism [editorial]. *J Neurol Neurosurg Psychiatry* (1997), 62: 305-9

Yamamura Y, Sobue I, Ando K, Iida M and Yanagi T. Paralysis agitans of early onset with marked diurnal fluctuation of symptoms. *Neurology* (1973), 23: 239-44

TABLE 1

| Nucleotide Position change | | Oligonucleotide sequence |
|---|---|---|
| Ex3 | 321-322insGT | WT: 5'TGCAGAGACC_GTGGAGAAAA-3' (SEQ ID No: 14)<br>V: 5'GCAGAGACCGTGTGGAGAAA-3' (SEQ ID No: 15) |

TABLE 1-continued

| Position | Nucleotide change | Oligonucleotide sequence |
|---|---|---|
| Ex4 | 584A > T | WT: 5'-GCCGGGAAAACTCAGGGTA-3' (SEQ ID No: 16)<br>V: 5'-GCCGGGAAATCTCAGGGTA-3' (SEQ ID No: 17) |
| Ex7 | 867C > T | WT: 5'-TGCAACTCCCGCCACGTGA-3' (SEQ ID No: 18)<br>V: 5'-TGCAACTCCTGCCACGTGA-3' (SEQ ID No: 19) |
| Ex10 | 1239G > C | WT: 5'-TGCAGTGCCGTATTTGAAG-3' (SEQ ID No: 20)<br>V: 5'-TGCAGTGCCCTATTTGAAG-3' (SEQ ID No: 21) |
| Ex11 | 1345C > A | WT: 5'-AGAAAACCACCAAGCCCTG-3' (SEQ ID No: 22)<br>V: 5'-AGAAAACCAACAAGCCCTG-3' (SEQ ID No: 23) |

TABLE 2

| | Nucleotide changed | Amino acid changed (position of the stop codon) | Type of mutation | Detection technique | Expected length of the fragment (bp) |
|---|---|---|---|---|---|
| Exon | | | | | |
| Ex2 | 202-203delAG | Gln34Arg(Stop37) | reading frame | PAGE | WT: 308<br>V: 306 |
| Ex2 | 255delA | Asn52Met(Stop81) | reading frame | Fok 1 creation of the site | WT: 278 + 30<br>V: 222 + 57 + 30 |
| Ex3 | 321-322insGT | Trp74Cys(Stop81) | reading frame | ASO | |
| Ex4 | 584A > T | Lys161Asn | missense (nonconservative) | ASO | |
| Ex4 | 601G > A | Ser167Asn | missense (nonconservative) | Alw NI loss of the site | WT: 164 + 97<br>V: 261 |
| Ex6 | 734A > T | Lys211Asn | missense (nonconservative) | Dra I loss of the site | WT: 171 + 98<br>V: 269 |
| Ex7 | 867C > T | Arg256Cys | missense (nonconservative) | ASO | |
| Ex7 | 905T > A | Cys268Stop | nonsense | Dde I gain of the site | WT: 141 + 100<br>V: 117 + 100 + 24 |
| Ex7 | 924C > T | Arg275Trp | missense (nonconservative) | Sau3A I loss of the site | WT: 142 + 97<br>V: 239 |
| Ex7 | 939G > A | Asp280Asn | missense (nonconservative) | Alw I with mismatched primer loss of the site | WT: 153 + 30<br>V: 183 |
| Ex7 | 966T > G | Cys289Gly | missense (nonconservative) | BstN I gain of the site | WT: 177 + 64<br>V: 118 + 64 + 59 |
| Ex9 | 1142-1143delGA | Arg348Glu(Stop368) | reading frame | PAGE | WT: 278<br>V: 276 |
| Ex9 | 1084G > A | Gly328Glu | missense (nonconservative) | Mnl I gain of the site | WT: 124 + 80 + 74<br>v: 124 + 74 + 60 + 20 |
| Ex9 | 1101C > T | Arg334Cys | missense (nonconservative) | BstU I with mismatched primer loss of the site | WT: 123 + 21<br>V: 144 |
| Ex10 | 1239G > C | Val380Leu | missense (conservative) | ASO | |
| Ex11 | 1281G > A | Asp394Asn | missense (nonconservative) | Taq I loss of the site | WT: 221 + 84<br>V: 303 |
| Ex11 | 1345C > A | Thr415Asn | missense (conservative) | ASO | |
| Ex12 | 1390G > A | Gly430Asp | missense (nonconservative) | Mnl I loss of the site | WT: 191 + 65<br>V: 256 |
| Ex12 | 1459G > A | Trp453Stop | nonsense | Nla IV loss of the site | WT: 142 + 17 + 35 + 61<br>V: 159 + 35 + 61 |
| intron | | | | | |
| Intron 2 | IVS2 + 25T > C (272 + 25T > C) | | | BstN I creation of the site | WT: 308 bp<br>V: 264 + 44 bp |
| Intron 3 | IVS3 − 20C > T (514 − 20C > T) | | | Mnl I loss of the site | WT: 201 + 60<br>V: 261 |
| Intron 7 | IVS7 − 35A > G (973 − 35A > G) | | | Mae III creation of the site | WT: 206<br>V: 159 + 47 |
| Intron 8 | IVS8-21-17del (1035-21-17del) TCTGC | splice site | | PAGE | |

TABLE 3

CLINICAL CHARACTERISTICS OF FAMILIES WITH MUTATIONS IN THE PARKIN GENE

|  | Homozygous deletions | Missense mutations | Truncating mutations | Total |
|---|---|---|---|---|
| Families (patients) | 3 (8) | 3 (8) | 4 (9) | 10 (25) |
| Average age at onset (extremes) | 30 ± 16 (7-55) | 44 ± 9 (30-56) | 37 ± 6 (29-45) | 37 ± 12 (7-56) |
| Average duration of evolution (extremes) | 13 ± 6 (3-20) | 13 ± 7 (0.5-27) | 16 ± 10 (3-29) | 14 ± 8 (0.5-29) |
| Hoehn and Yahr scale | 3.1 ± 1.2 | 2.6 ± 0.8 | 2.0 ± 0.6 | 2.5 ± 0.98 |
| Akinesia | 8/8 | 8/8 | 8/9 | 96% |
| Rigidity | 8/8 | 8/8 | 9/9 | 100% |
| Tremor | 3/8 | 4/8 | 8/9 | 60% |
| Dystonia | 4/8 | 0/5 | 1/7 | 25% |
| Good reaction to levodopa (case de novo) | 7/7 (1) | 6/6 (2) | 7/7 | 100% |
| Dyskinesia | 4/7 | 5/6 | 6/9 | 68% |
| Fluctuations[a] | 7/7 | ND | 2/6 | 62% |
| Sharp reflexes in the lower limbs | 2/8 | 3/4 | 0/6 | 28% |

TABLE 4

| exon(s) deleted/multiplied | Number of families | Consequences |
|---|---|---|
| 2 del | 3 × het | Reading frame shift |
| 2 triplication | 1 × hom + 1 × het | No reading frame shift |
| 2 + 3 del | 1 × het | No reading frame shift |
| 2 + 3 + 4 del | 1 × het | Reading frame shift |
| 3 del | 3 × hom + 7 × het | Reading frame shift |
| 3 duplication | 1 × hom + 1 × het | Reading frame shift |
| 3 + 4 del | 1 × hom + 3 × het | No reading frame shift |
| 3 – 6 del | 1 × het | Reading frame shift |
| 3 – 9 del | 1 × het | No reading frame shift |
| 4 del | 1 × hom + 3 × het | Reading frame shift |
| 5 del | 3 × het | No reading frame shift |
| 5 + 6 del | 2 × hom | Reading frame shift |
| 6 del | 1 × het | Reading frame shift |
| 6 duplication | 1 × het | Reading frame shift |
| 6 + 7 del | 1 × het | Reading frame shift |
| 7 duplication | 1 × het | Reading frame shift |
| 7 + 8 + 9 del | 1 × het | Reading frame shift |
| 8 del | 1 × het | Reading frame shift |
| 8 + 9 del | 1 × hom | Reading frame shift |
| 11 duplication | 1 × het | Reading frame shift |

TABLE 5

| Case | 3i | 12 | 9 | 2 | C328 | C328/3i | C328/12 | C328/9 | C328/2 | Ex3i/12 | Ex3i/9 | Ex3i/2 | Ex12/9 | EX12/2 | Ex9/2 |
|---|---|---|---|---|---|---|---|---|---|---|---|---|---|---|---|
| T2 | 743 | 838 | 1040 | 935 | 455 | 0.61 | 0.54 | 0.44 | 0.49 | 0.89 | 0.71 | 0.79 | 0.81 | 0.90 | 1.11 |
| FR 155 5 | 608 | 1245 | 1588 | 1466 | 635 | 1.04 | 0.51 | 0.40 | 0.43 | 0.49 | 0.38 | 0.41 | 0.78 | 0.85 | 1.08 |
| T2/FR 155 5 |  |  |  |  |  | 0.59 | 1.06 | 1.09 | 1.12 | 1.82 | 1.87 | 1.92 | 1.03 | 1.06 | 1.03 |
| FR 155 6 | 759 | 861 | 1120 | 540 | 498 | 0.66 | 0.58 | 0.44 | 0.92 | 0.88 | 0.68 | 1.41 | 0.77 | 1.59 | 2.07 |
| T2/FR 155 6 |  |  |  |  |  | 0.93 | 0.94 | 0.98 | 0.53 | 1.01 | 1.05 | 0.57 | 1.05 | 0.56 | 0.54 |
| FR 155 8 | 597 | 1185 | 1467 | 766 | 623 | 1.04 | 0.53 | 0.42 | 0.81 | 0.50 | 0.41 | 0.78 | 0.81 | 1.55 | 1.92 |
| T2/FR 155 8 |  |  |  |  |  | 0.59 | 1.03 | 1.03 | 0.60 | 1.76 | 1.76 | 1.02 | 1.00 | 0.58 | 0.58 |
| FR 155 9 | 495 | 1200 | 1438 | 754 | 688 | 1.39 | 0.57 | 0.48 | 0.91 | 0.41 | 0.34 | 0.66 | 0.83 | 1.59 | 1.91 |
| T2/FR 155 9 |  |  |  |  |  | 0.44 | 0.95 | 0.91 | 0.53 | 2.15 | 2.08 | 1.21 | 0.97 | 0.56 | 0.58 |

The invention claimed is:

1. A method for the identification of a genetic alteration in a parkin gene in a subject, comprising: i) contacting one or more detectably labeled oligonucleotides with a parkin nucleic acid in a biological sample from a subject, wherein the oligonucleotide specifically hybridizes to a sequence comprising a genetic alteration in said parkin nucleic acid, and ii) detecting hybridization of the one or more oligonucleotides with said parkin nucleic acid, thereby identifying a genetic alteration in a parkin gene in the subject upon detection of hybridization in step ii), wherein said genetic alteration in said parkin gene is selected from the group consisting of: a) a deletion of one or more exons selected from the group consisting of: exon 2, exons 2-3, exons 2-4, exons 3-4, exons 3-6, exons 3-9, exon 5, exons 5-6, exon 6, exons 6-7, exons 7-9, and exon 8; b) a multiplication of exons selected from the group consisting of: a triplication of exon 2, a duplication of exon 3, a duplication of exon 6, a duplication of exon 7, and a duplication of exon 11; c) a point mutation selected from the group consisting of: a mutation from adenine to thymine at a position corresponding to position 584 of SEQ ID NO:1, a mutation from guanine to adenine at a position corresponding to position 601 of SEQ ID NO:1, a mutation from adenine to thymine at a position corresponding to position 734 of SEQ ID NO:1, a mutation from cytosine to thymine at a position corresponding to position 867 of SEQ ID NO:1, a mutation from thymine to adenine at a position corresponding to position 905 of SEQ ID NO:1, a mutation from cytosine to thymine at a position corresponding to position 924 of SEQ ID NO:1, a mutation from guanine to adenine at a position corresponding to position 939 of SEQ ID NO:1, a mutation from thymine to guanine at a position corresponding to position 966 of SEQ ID NO:1, a mutation from guanine to adenine at a position corresponding to position 1084 of SEQ ID NO:1, a mutation from cytosine to thymine at a position corresponding to position 1101 of SEQ ID NO1, a mutation from guanine to cytosine at a position corresponding to position 1239 of SEQ ID NO:1, a mutation from guanine to adenine at a position corresponding to position 1281 of SEQ ID NO:1, a mutation from cytosine to adenine at a position corresponding to position 1345 of SEQ ID NO:1, a mutation from guanine to adenine at a position corresponding to position 1390 of SEQ ID NO:1, and a mutation from guanine to adenine at a position corresponding to position 1459 of SEQ ID NO:1; d) a deletion of 1 or more contiguous base pairs selected from the group consisting of: a deletion of nucleotides adenine and guanine at positions corresponding to positions 202-203 of SEQ ID NO:1, a deletion of adenine at a position corresponding to position 255 of SEQ ID NO:1, and a deletion of nucleotides guanine and adenine at positions corresponding to positions 1142-1143 of SEQ ID NO:1; or e) an insertion of 1 or more contiguous base pairs selected from the group consisting of: an insertion of guanine and thymine at positions corresponding to 321-322 of SEQ ID NO:1.

2. The method of claim 1, wherein the biological sample comprises blood, tissue, plasma or a cell culture from said subject.

3. The method of claim 1, wherein the genetic alteration comprises a point mutation that results in a nonsense mutation.

4. The method of claim 3, wherein the nonsense mutation affects exon 7, exon 12, or a combination thereof.

5. The method of claim 3, wherein the point mutation comprises the point mutation 905T>A that introduces a stop codon at a position corresponding to the Cys268 residue encoded by the sequence of SEQ ID NO: 1, or the point mutation 1459G>A that introduces a stop codon at a position corresponding to the Trp453 residue encoded by the sequence of SEQ ID NO: 1.

6. The method of claim 1, wherein the genetic alteration is a point mutation that results in a missense mutation.

7. The method of claim 6, wherein the missense mutation causes a nonconservative change in the amino acid sequence encoded by the sequence of SEQ ID NO:1.

8. The method of claim 6, wherein the missense mutation comprises a point mutation selected from the group consisting of 584A>T at a position corresponding to SEQ ID NO: 1 (Lys161Asn), 601G>A T at a position corresponding to SEQ ID NO:1 (Ser167Asn), 734A>T at a position corresponding to SEQ ID NO:1 (Lys211Asn), 867C>T T at a position corresponding to SEQ ID NO:1 (Arg256Cys), 924C>T at a position corresponding to SEQ ID NO:1 (Arg275Trp), 939G>A at a position corresponding to SEQ ID NO:1 (Asp280Asn), 966T>G (Cys289Gly), 1084G>A at a position corresponding to SEQ ID NO:1 (Gly328Glu), 1101C>T at a position corresponding to SEQ ID NO:1 (Arg334Cys), 1281G>A T at a position corresponding to SEQ ID NO:1 (Asp394Asn), and 1390G>A T at a position corresponding to SEQ ID NO:1 (Gly430Asp).

9. The method of claim 6, wherein the missense mutation causes a conservative change in the amino acid sequence encoded by the sequence of SEQ ID NO: 1.

10. The method of claim 9, wherein the missense mutation comprises a point mutation selected from the group consisting of 1239G >C T at a position corresponding to SEQ ID NO:1 (Val380Leu) and 1345C>A T at a position corresponding to SEQ ID NO:1 (Thr415Asn).

11. The method of claim 9, wherein the missense mutation affects a potential phosphorylation site of a polypeptide encoded by said isolated nucleic acid molecule.

12. The method of claim 10, wherein the point mutation is Thr415Asn.

13. The method of claim 1, wherein the genetic alteration comprises a deletion of one or more contiguous base pair(s) that causes a reading frame shift.

14. The method of claim 13, wherein the deletion is selected from the group consisting of: a deletion of the nucleotides adenine and guanine at positions corresponding to positions 202-203 of SEQ ID NO:1, a deletion of the nucleotide adenine at a position corresponding to position 255 of SEQ ID NO:1, and a deletion of the nucleotides guanine and adenine at positions corresponding to positions 1142-1143 of SEQ ID NO:1.

15. The method of claim 1, wherein the genetic alteration comprises an insertion of one or more contiguous base pair(s) that causes a reading frame shift.

16. The method of claim 15, wherein the insertion is an insertion of nucleotides guanine and thymine at positions corresponding to positions 321-322 of SEQ ID NO:1.

17. The method of claim 1, wherein the method further comprises performing semi-quantitative multiplex PCR.

18. The method of claim 1, wherein the one or more detectably labeled oligonucleotides are detectably labeled with a radioactive, fluorescent, enzymatic, chemical, end and/or internal label.

* * * * *

```
                      SEQUENCE LISTING

<160> NUMBER OF SEQ ID NOS: 23

<210> SEQ ID NO 1
<211> LENGTH: 2960
<212> TYPE: DNA
<213> ORGANISM: Homo sapiens

<400> SEQUENCE: 1
tccgggagga ttacccagga gaccgctggt gggaggcgcg gctggcgccg ctgcgcgcat      60
gggcctgttc ctggcccgca gccgccacct acccagtgac catgatagtg tttgtcaggt     120
tcaactccag ccatggtttc ccagtggagg tcgattctga caccagcatc ttccagctca     180
aggaggtggt tgctaagcga caggggttc cggctgacca gttgcgtgtg attttcgcag     240
ggaaggagct gaggaatgac tggactgtgc agaattgtga cctggatcag cagagcattg     300
ttcacattgt gcagagaccg tggagaaaag gtcaagaaat gaatgcaact ggaggcgacg     360
```

```
accccagaaa cgcggcggga ggctgtgagc gggagcccca gagcttgact cgggtggacc      420
tcagcagctc agtcctccca ggagactctg tggggctggc tgtcattctg cacactgaca      480
gcaggaagga ctcaccacca gctggaagtc cagcaggtag atcaatctac aacagctttt      540
atgtgtattg caaaggcccc tgtcaaagag tgcagccggg aaaactcagg gtacagtgca      600
gcacctgcag gcaggcaacg ctcaccttga cccagggtcc atcttgctgg gatgatgttt      660
taattccaaa ccggatgagt ggtgaatgcc aatccccaca ctgccctggg actagtgcag      720
aatttttctt taaatgtgga gcacacccca cctctgacaa ggaaacatca gtagctttgc      780
acctgatcgc aacaaatagt cggaacatca cttgcattac gtgcacagac gtcaggagcc      840
ccgtcctggt tttccagtgc aactcccgcc acgtgatttg cttagactgt ttccacttat      900
actgtgtgac aagactcaat gatcggcagt tgttcacga ccctcaactt ggctactccc       960
tgccttgtgt ggctggctgt cccaactcct tgattaaaga gctccatcac ttcaggattc     1020
tgggagaaga gcagtacaac cggtaccagc agtatggtgc agaggagtgt gtcctgcaga     1080 tgggggggcgt gttatgcccc cgccctggct gtggagcggg gctgctgccg gagcctgacc     1140
agaggaaagt cacctgcgaa gggggcaatg gcctgggctg tgggtttgcc ttctgccggg     1200
aatgtaaaga agcgtaccat gaaggggagt gcagtgccgt atttgaagcc tcaggaacaa     1260
ctactcaggc ctacagagtc gatgaaagag ccgccgagca ggctcgttgg gaagcagcct     1320
ccaaagaaac catcaagaaa accaccaagc cctgtcccg ctgccatgta ccagtggaaa      1380
aaaatggagg ctgcatgcac atgaagtgtc cgcagcccca gtgcaggctc gagtggtgct     1440
ggaactgtgg ctgcgagtgg aaccgcgtct gcatgggga ccactggttc gacgtgtagc      1500
cagggcggcc gggcgcccca tcgccacatc ctggggagc ataccagtg tctaccttca      1560 ttttctaatt ctcttttcaa acacacacac acgcgcgc gcgcgcacac acactcttca      1620 agttttttc aaagtccaac tacagccaaa ttgcagaaga aactcctgga tcccttcac      1680 tatgtccatg aaaaacagca gagtaaaatt acagaagaag ctcctgaatc cctttcagtt     1740
tgtccacaca agacagcaga gccatctgcg acaccaccaa caggcgttct cagcctccgg     1800
atgacacaaa taccagagca cagattcaag tgcaatccat gtatctgtat gggtcattct     1860
cacctgaatt cgagacaggc agaatcagta gctggagaga gagttctcac atttaatatc     1920 ctgccttta ccttcagtaa acaccatgaa gatgccattg acaaggtgtt tctctgtaaa      1980
atgaactgca gtgggttctc caaactagat tcatggcttt aacagtaatg ttcttattta     2040
aattttcaga aagcatctat tcccaaagaa ccccaggcaa tagtcaaaaa catttgttta     2100
tccttaagaa ttccatctat ataaatcgca ttaatcgaaa taccaactat gtgtaaatca     2160
acttgtcaca aagtgagaaa ttatgaaagt taatttgaat gttgaatgtt tgaattacag     2220
ggaagaaatc aagttaatgt actttcattc cctttcatga tttgcaactt tagaaagaaa     2280 ttgttttct gaaagtatca ccaaaaaatc tatagtttga ttctgagtat tcattttgca      2340
acttggagat tttgctaata catttggctc cactgtaaat ttaatagata aagtgcctat     2400
aaaggaaaca cgtttagaaa tgatttcaaa atgatattca atcttaacaa aagtgaacat     2460
tattaaatca gaatctttaa agaggagcct ttccagaact accaaaatga agacacgccc     2520
gactctctcc atcagaaggg tttatacccc tttggcacac cctctctgtc caatctgcaa     2580
gtcccaggga gctctgcata ccaggggttc cccaggagag accttctctt aggacagtaa     2640
actcactaga atattcctta tgttgacatg gattggattt cagttcaatc aaactttcag     2700
cttttttttc agccattcac aacacaatca aaagattaac aacactgcat gcggcaaacc     2760
```

```
gcatgctctt acccacacta cgcagaagag aaagtacaac cactatcttt tgttctacct    2820
gtattgtctg acttctcagg aagatcgtga acataactga gggcatgagt ctcactagca    2880
catggaggcc cttttggatt tagagactgt aaattattaa atcggcaaca gggcttctct    2940
ttttagatgt agcactgaaa                                                2960

<210> SEQ ID NO 2
<211> LENGTH: 19
<212> TYPE: DNA
<213> ORGANISM: Homo sapiens

<400> SEQUENCE: 2
aattgtgacc tggatcagc                                                   19

<210> SEQ ID NO 3
<211> LENGTH: 23
<212> TYPE: DNA
<213> ORGANISM: Homo sapiens

<400> SEQUENCE: 3
ctggacttcc agctggtggt gag                                              23

<210> SEQ ID NO 4
<211> LENGTH: 25
<212> TYPE: DNA
<213> ORGANISM: Homo sapiens

<400> SEQUENCE: 4
ggcagggagt agccaagttg aggat                                            25

<210> SEQ ID NO 5
<211> LENGTH: 22
<212> TYPE: DNA
<213> ORGANISM: Homo sapiens

<400> SEQUENCE: 5
agccccgctc cacagccagc gc                                               22

<210> SEQ ID NO 6
<211> LENGTH: 19
<212> TYPE: DNA
<213> ORGANISM: Homo sapiens

<400> SEQUENCE: 6
aattgtgacc tggatcagc                                                   19

<210> SEQ ID NO 7
<211> LENGTH: 23
<212> TYPE: DNA
<213> ORGANISM: Homo sapiens

<400> SEQUENCE: 7
ctggacttcc agctggtggt gag                                              23

<210> SEQ ID NO 8
<211> LENGTH: 19
<212> TYPE: DNA
<213> ORGANISM: Homo sapiens

<400> SEQUENCE: 8
aattgtgacc tggatcagc                                                   19
```

```
<210> SEQ ID NO 9
<211> LENGTH: 23
<212> TYPE: DNA
<213> ORGANISM: Homo sapiens

<400> SEQUENCE: 9
ctggacttcc agctggtggt gag                                            23

<210> SEQ ID NO 10
<211> LENGTH: 20
<212> TYPE: DNA
<213> ORGANISM: Homo sapiens

<400> SEQUENCE: 10
acgttcctga taatgggatc                                                20

<210> SEQ ID NO 11
<211> LENGTH: 20
<212> TYPE: DNA
<213> ORGANISM: Homo sapiens

<400> SEQUENCE: 11
cctctctcta ccaagtgagg                                                20

<210> SEQ ID NO 12
<211> LENGTH: 25
<212> TYPE: DNA
<213> ORGANISM: Homo sapiens

<400> SEQUENCE: 12
ggcagggagt agccaagttg aggat                                          25

<210> SEQ ID NO 13
<211> LENGTH: 22
<212> TYPE: DNA
<213> ORGANISM: Homo sapiens

<400> SEQUENCE: 13
agccccgctc cacagccagc gc                                             22

<210> SEQ ID NO 14
<211> LENGTH: 20
<212> TYPE: DNA
<213> ORGANISM: Homo sapiens

<400> SEQUENCE: 14
tgcagagacc gtggagaaaa                                                20

<210> SEQ ID NO 15
<211> LENGTH: 20
<212> TYPE: DNA
<213> ORGANISM: Homo sapiens

<400> SEQUENCE: 15
gcagagaccg tgtggagaaa                                                20

<210> SEQ ID NO 16
<211> LENGTH: 19
<212> TYPE: DNA
<213> ORGANISM: Homo sapiens

<400> SEQUENCE: 16
gccgggaaaa ctcagggta                                                 19
```

```
<210> SEQ ID NO 17
<211> LENGTH: 19
<212> TYPE: DNA
<213> ORGANISM: Homo sapiens

<400> SEQUENCE: 17
gccgggaaat ctcagggta                                                  19

<210> SEQ ID NO 18
<211> LENGTH: 19
<212> TYPE: DNA
<213> ORGANISM: Homo sapiens

<400> SEQUENCE: 18
tgcaactccc gccacgtga                                                  19

<210> SEQ ID NO 19
<211> LENGTH: 19
<212> TYPE: DNA
<213> ORGANISM: Homo sapiens

<400> SEQUENCE: 19
tgcaactcct gccacgtga                                                  19

<210> SEQ ID NO 20
<211> LENGTH: 19
<212> TYPE: DNA
<213> ORGANISM: Homo sapiens

<400> SEQUENCE: 20
tgcagtgccg tatttgaag                                                  19

<210> SEQ ID NO 21
<211> LENGTH: 19
<212> TYPE: DNA
<213> ORGANISM: Homo sapiens

<400> SEQUENCE: 21
tgcagtgccc tatttgaag                                                  19

<210> SEQ ID NO 22
<211> LENGTH: 19
<212> TYPE: DNA
<213> ORGANISM: Homo sapiens

<400> SEQUENCE: 22
agaaaaccac caagccctg                                                  19

<210> SEQ ID NO 23
<211> LENGTH: 19
<212> TYPE: DNA
<213> ORGANISM: Homo sapiens

<400> SEQUENCE: 23
agaaaaccaa caagccctg                                                  19
```